US010155219B2

(12) United States Patent
Choi et al.

(10) Patent No.: US 10,155,219 B2
(45) Date of Patent: Dec. 18, 2018

(54) CATALYST CONTAINING METAL CLUSTER IN STRUCTURALLY COLLAPSED ZEOLITE, AND USE THEREOF

(71) Applicants: SK INNOVATION CO., LTD., Seoul (KR); KOREA ADVANCED INSTITUTE OF SCIENCE AND TECHNOLOGY, Daejeon (KR)

(72) Inventors: Min Kee Choi, Daejeon (KR); Ju Hwan Im, Busan (KR); Do Woan Kim, Daejeon (KR); Do Kyoung Kim, Daejeon (KR); Tae Jin Kim, Seoul (KR); Seung Hoon Oh, Seoul (KR); Tae Hong Seok, Daejeon (KR)

(73) Assignees: SK INNOVATION CO., LTD., Seoul (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 167 days.

(21) Appl. No.: 14/784,214

(22) PCT Filed: Apr. 22, 2014

(86) PCT No.: PCT/KR2014/003491
§ 371 (c)(1),
(2) Date: Oct. 13, 2015

(87) PCT Pub. No.: WO2014/175626
PCT Pub. Date: Oct. 30, 2014

(65) Prior Publication Data
US 2016/0051971 A1 Feb. 25, 2016

(30) Foreign Application Priority Data

Apr. 22, 2013 (KR) .................. 10-2013-0044357
Apr. 17, 2014 (KR) .................. 10-2014-0045750

(51) Int. Cl.
*B01J 29/06* (2006.01)
*B01J 29/12* (2006.01)
*C01B 39/02* (2006.01)
*B01J 29/72* (2006.01)
*B01J 29/76* (2006.01)
*C01B 39/22* (2006.01)
*B01J 37/08* (2006.01)
*B01J 29/14* (2006.01)
*B01J 29/10* (2006.01)
*B01J 29/08* (2006.01)
*B01J 29/70* (2006.01)
*B01J 29/74* (2006.01)
*B01J 37/02* (2006.01)
(Continued)

(52) U.S. Cl.
CPC ........... *B01J 29/123* (2013.01); *B01J 29/082* (2013.01); *B01J 29/103* (2013.01); *B01J 29/143* (2013.01); *B01J 29/7003* (2013.01);
*B01J 29/7207* (2013.01); *B01J 29/74* (2013.01); *B01J 29/7407* (2013.01); *B01J 29/7607* (2013.01); *B01J 37/0201* (2013.01); *B01J 37/08* (2013.01); *B01J 37/082* (2013.01); *B01J 37/088* (2013.01); *C01B 39/026* (2013.01); *C01B 39/14* (2013.01); *C01B 39/22* (2013.01); *C07C 5/3337* (2013.01); *C07C 5/367* (2013.01); *C10G 3/42* (2013.01); *C10G 3/49* (2013.01); *C10G 45/00* (2013.01); *C10G 45/04* (2013.01); *C10G 45/12* (2013.01); *C10G 45/60* (2013.01); *C10G 45/64* (2013.01); *C10G 45/68* (2013.01); *B01J 29/08* (2013.01); *B01J 2229/186* (2013.01); *B01J 2229/40* (2013.01); *Y02P 30/20* (2015.11)

(58) Field of Classification Search
CPC ...... B01J 29/7003; B01J 29/082; B01J 29/74; B01J 29/123; B01J 29/7407; B01J 29/08; B01J 29/7207; B01J 29/7607; B01J 29/103; B01J 29/143; B01J 2229/186; B01J 2229/40; B01J 37/082; B01J 37/08; B01J 37/0201; B01J 37/088; C10G 45/12; C10G 45/64; C10G 3/49; C01B 39/14; C01B 37/22; C01B 39/026; C01B 39/22
USPC .......................... 502/60, 74, 79, 85
See application file for complete search history.

(56) References Cited

U.S. PATENT DOCUMENTS 3,764,520 A * 10/1973 Kimberlin, Jr. .......... B01J 29/80
208/111.15
4,582,650 A * 4/1986 Felthouse ................ B01J 23/40
502/74
(Continued)

FOREIGN PATENT DOCUMENTS

| KR | 1020000016112 A | 3/2000 |
| KR | 1020000058174 A | 9/2000 |
| WO | 2012/140675 A1 | 10/2012 |

OTHER PUBLICATIONS

Choi et al. Mercaptosilane-Assisted Synthesis of Metal Clusters within Zeolites and Catalytic Consequences of Encapsulation. Jun. 10, 2010. JACS, vol. 132, pp. 9129-9137.*
(Continued)

Primary Examiner — Elizabeth D Wood
(74) Attorney, Agent, or Firm — Abelman, Frayne & Schwab

(57) ABSTRACT

This invention relates to a hydrogen spillover-based catalyst and use thereof, wherein a hydrogen activation metal cluster is dispersed in the form of being encapsulated in a crystalline or amorphous aluminosilicate matrix which is partially or fully structurally collapsed zeolite, thereby exhibiting high hydroprocessing or dehydrogenation activity and suppressed C—C hydrogenolysis activity.

8 Claims, 15 Drawing Sheets

(51) Int. Cl.

| | |
|---|---|
| *C07C 5/333* | (2006.01) |
| *C07C 5/367* | (2006.01) |
| *C10G 45/00* | (2006.01) |
| *C10G 45/12* | (2006.01) |
| *C10G 45/64* | (2006.01) |
| *C10G 45/04* | (2006.01) |
| *C10G 45/60* | (2006.01) |
| *C10G 45/68* | (2006.01) |
| *C10G 3/00* | (2006.01) |
| *C01B 39/14* | (2006.01) |

(56) References Cited

U.S. PATENT DOCUMENTS

| | | | | |
|---|---|---|---|---|
| 4,912,072 | A * | 3/1990 | Mallouk | B01J 29/068 502/66 |
| 5,847,652 | A * | 12/1998 | Yamamoto | G08B 15/004 340/384.3 |
| 6,410,473 | B1 * | 6/2002 | Pinnavaia | B01J 29/0308 423/277 |
| 6,887,814 | B2 * | 5/2005 | Herbst | B01J 29/061 502/60 |
| 7,153,806 | B2 | 12/2006 | Ring | |
| 7,306,824 | B1 * | 12/2007 | Coker | B82Y 30/00 427/115 |
| 2009/0048094 | A1 * | 2/2009 | Ring | B01J 29/068 502/74 |

OTHER PUBLICATIONS

Choi, M. et al., "Mercaptosilane-Assisted Synthesis of Metal Clusters within Zeolites and Catalytic Consequences of Encapsulation"; JASC, vol. 132, pp. 913 (2010).

Passos, Fabio, B., Effect of In and Sn on the Adsorption Behavior and Hydrogenolyis Activity of Pt/Al2O3 Catalysts; Journal of Catalysts 160, 106-117 (1996).

Menon, Govind, P.; "Some Aspects of the Mechanisms of Catalytic Reforming Reactions", Ind. Eng. Chem. Res. 1997, 3282-3291.

Song, Chunshan; Zeolite-Supported Pd and Pt Catalysts for Low-Temperature Hydrogenation of Naphthalene in the Absence and Presence of Benzothiophene; Energy & Fuels; 1997, 656-661.

International Search Report for International Application No. PCT/KR2014/003491 dated Jul. 22, 2014.

Supplementary European Search Report for Application EP 14 78 8913 dated Dec. 8, 2016 (15 pages).

P. Gallezot, et al., "Location and dispersion of platinum in PtY zeolites," Journal of Catalysis, 39:3:334-349 (Sep. 1, 1975).

Hong Yang, et al., "Incorporating platinum precursors into a NeA-zeolite synthesis mixture promoting the formation of nanosized zeolite," Microporous and Mesoporous Materials, 117:1-2:33-40 (Jan. 1, 2009).

Minkee Choi, et al., "MErcaptosilane-Assisted Synthesis of Metal Clusters within Zeolites and Catalytic Consequences of Encapsulation," Journal of the American Chemical Society, 132:26:9129-9137 (Jul. 7, 2010).

Mirza Aqueel Balg, et al., "IMECE2011-53655 Synthesis of Zeolite A Crystals in the Presence of Crystal Growth Inhibitors by Microwave-Assisted Hydrothermal Technique," Retrieved from the Internet: URL:http://citeseerx.ist.psu.edu/viewdoc/download?doi=10.1.1.550.8199&rep=repl&type=pdf (Jan. 1, 2011).

Hirohisa Yamada, et al., "Micro-cubic glass from pseudomorphism after thermal treatment of ammonium-exchanged zeolite A," Science and Technology of Advanced Materials, 6:3-4:394-398 (Apr. 1, 2005).

Toru Wakihara, et al., "Changes in ten medium-range order of zeolite A by mechanical and thermal amorphization," Microporous and Mesoporous Materials, 136:1-3:1387-1811 (Dec. 1, 2010).

Bi-Zang Zhan, et al., "RuO2 Clusters within LTA Zeolite Cages: Consequences of Encapsulation on Catalytic Reactivity and Selectivity," Angewandte Chemie International Edition, 46:20:3697-3700 (May 11, 2007).

Song Chen, et al., "In-situ Synthesis of Zeolite with Encapsulated Pt and Its Hydrogenation Activity at High Levels of Sulfur," Proceedings of the World Congress on Engineering and Computer Science, II:706-709, Retiieved from the Internet: URL/http://www.iaeng.org/publication/WCECS2010/WCECS2010_pp706-709.pdf.

* cited by examiner

Pt/Na ZEOLITE → STRUCTURAL COLLAPSE → Pt/ALUMINOSILICATE (PARTIAL OR FULL STRUCTURAL COLLAPSE OF ZEOLITE)

| Samples | Pt loading (wt%) | Na/Al | BET surface area ($m^2 g^{-1}$) | Chemisorption at 323 K | |
|---|---|---|---|---|---|
| | | | | H/Pt | CO/Pt |
| Pt/NaA-0 | 0.99 | 1.01 | 3 | 0.49 | 0.48 |
| Pt/NaHA-0 | 1.02 | 0.55 | 3 | 0.11 | 0.03 |
| Pt/HA-0 | 1.01 | 0.07 | 2 | 0.00 | 0.00 |
| Pt/NaA-0.24 | 1.01 | 0.99 | 18 | 0.41 | 0.51 |
| Pt/NaHA-0.24 | 1.02 | 0.54 | 15 | 0.07 | 0.05 |
| Pt/HA-0.24 | 1.00 | 0.06 | 12 | 0.02 | 0.01 |
| Pt/NaA-0.95 | 0.98 | 1.00 | 38 | 0.38 | 0.46 |
| Pt/NaHA-0.95 | 0.98 | 0.56 | 34 | 0.10 | 0.11 |
| Pt/HA-0.95 | 1.02 | 0.07 | 33 | 0.00 | 0.01 |
| Pt/SiO$_2$ | 1.00 | - | - | 0.51 | 0.44 | ns
CATALYST CONTAINING METAL CLUSTER IN STRUCTURALLY COLLAPSED ZEOLITE, AND USE THEREOF

CROSS-REFERENCE TO RELATED APPLICATIONS

This application is a National Phase of PCT/KR2014/003491, filed Apr. 22, 2014, which claims priority from Korean Application No. 10-2013-0044357, filed Apr. 22, 2013 and Korean Application No. 10-2014-0045750, filed Apr. 17, 2014, the disclosures of which are all incorporated herein by reference.

TECHNICAL FIELD

The present invention relates to a hydrogen spillover-based catalyst having a metal cluster encapsulated in structurally collapsed zeolite, and to use thereof. More particularly, the present invention relates to a hydrogen spillover-based catalyst wherein a hydrogen activation metal cluster is dispersed in a crystalline or amorphous aluminosilicate matrix which is partially or fully structurally collapsed zeolite to thus attain high hydroprocessing or dehydrogenation activity and suppressed C—C hydrogenolysis activity, and to use thereof.

BACKGROUND ART

Recently, thorough research into use of heavy oil having high aromatic content while containing large amounts of heteroatoms such as sulfur and nitrogen is ongoing, and also the demand for a middle distillate which is the feed for transport fuel is increasing. Especially, hydroprocessing in a refining process, including hydrogenation, hydrodesulfurization (HDS), hydrodenitrogenation (HDN), etc. is regarded as important.

As the catalyst useful for such hydroprocessing, there is required to develop a catalyst which exhibits high hydroprocessing activity even in the presence of an impurity such as sulfur (acting as a catalyst poison), and also suppresses C—C bond cleavage (hydrogenolysis) to thereby inhibit production of hydrocarbons having comparatively low value due to a decrease in the number of carbons. The catalyst for hydroprocessing may include molybdenum sulfide such as NiMo, CoMo, etc. and a precious metal such as platinum (Pt), palladium (Pd), etc., which are currently widely used. In this regard, a molybdenum sulfide-based catalyst is known to have lower activity but to be more resistant to sulfur, compared to a precious metal-based catalyst. On the other hand, the precious metal-based catalyst shows high activity in the absence of sulfur but suffers from being rapidly deactivated in the presence of sulfur.

Meanwhile, in order to suppress hydrogenolysis during hydroprocessing, formation of an alloy such as Pt—Sn, Pt—In, etc. (F. B. Passos et al., J. Catal., 160:106, 1996), or partial poisoning of the surface of metal with a catalyst poison such as sulfur (P. Govind Menon, Eng. Chem. Res., 36:3282, 1997) has been studied. However, such methods are problematic because molecular sulfur has to be continuously added to the feed and byproducts may be generated by the added sulfur.

An alternative to the method of overcoming limitations of the conventional precious metal-based hydroprocessing catalyst, for example, supporting of metal particles in microporous (pore diameter of less than 1 nm) zeolite to thus enhance stability is under study. Specifically, C. Song et al. have researched hydrogenation of naphthalene in the presence of a sulfur compound after supporting of Pt in mordernite type zeolite (C. Song et al., Energy & Fuels, 11:656, 1997). It was reported that mordernite has two cages with different sizes, wherein hydrogenation is carried out only on Pt supported in the cage having a large size to which an organic molecule is accessible, and only hydrogen may be selectively diffused and activated on Pt supported in the cage having a small size, so that the activated hydrogen atom may move to Pt supported in the cage having a large size through a spillover phenomenon to thereby suppress deactivation of metal. However, as hydrogen sulfide ($H_2S$) produced upon decomposition of a sulfur compound diffuses into the cage having a small size, the metal in the cage having a small size may also become deactivated, and thus the effects thereof are limited.

In a study conducted by Hong Yang et al., A-type zeolite having Pt supported therein was used as a catalyst for hydrogenation of naphthalene (Hong Yang et al., J. Catal., 243:36, 2006; US Patent Publication NO. 2009/0048094). Specifically, the catalyst was designed such that, as a result of decreasing the final pore size of a zeolite cage up to about 2.9~3.5 Å by incorporating precious metal nanoparticles in the zeolite cage and then performing post-treatment (CVD, CLD, cation exchange or combination thereof), only molecular hydrogen may pass through the pores but an organic sulfur molecule ($H_2S$ having a kinematic diameter of 3.6 Å) cannot pass through the pores to thereby suppress contacting of the precious metal component with the poisoning material, that is, the sulfur compound. By means of such a catalytic structure, activated hydrogen (i.e. dissociated hydrogen) by precious metal undergoes spillover through the zeolite pores to thus induce hydrogenation, and may recycle the catalyst therearound (the sulfur compound which poisoned catalyst sites is removed by hydrogen). Furthermore, such researchers have made attempts to decrease the pore size by supporting Pt in A-type zeolite and then performing ion-exchange with $K^+$ and coating with silica. It was reported that the catalyst thus synthesized enables naphthalene, which cannot diffuse into zeolite pores, to be successfully hydrogenated through spillover of activated hydrogen, and is very resistant to sulfur.

In a study conducted by Chen et al., hydroprocessing reactivity for actual crude oil reactants containing diverse sulfur compounds was measured using P-type zeolite having Pt supported therein, in which P-type zeolite has a smaller pore size than A-type zeolite (Song Chen et al., Proceedings of the World Congress on Engineering and Computer Science, vol. 2, 2010). This paper proposed the catalyst to be configured such that Pt is encapsulated in the sodalite cage of P-type zeolite on the basis of shape selectivity and hydrogen spillover principle. In this case, $H_2$ passes through the pores, whereas $H_2S$ does not. Hence, even when such a catalyst is exposed to a high sulfur-containing environment, hydroprocessing activity thereof may be maintained.

Despite the above research results, there are still needs for hydrogen spillover-based catalysts which exhibit further improved catalytic activity in the art.

DISCLOSURE

Technical Problem

Therefore, an embodiment of the present invention is intended to provide a hydrogen spillover-based catalyst and a preparation method thereof, wherein a zeolite crystal structure containing a metal cluster is partially or fully collapsed, and thereby the activity distinct from a conventional catalyst may be attained.

Also, another embodiment of the present invention is intended to provide a hydrogen spillover-based catalyst and a preparation method thereof, wherein the catalyst may exhibit high hydroprocessing activity, may suppress C—C bond cleavage, and may ensure superior thermal stability.

Technical Solution

According to a first aspect of the present invention, a hydrogen spillover-based catalyst includes crystalline or amorphous aluminosilicate formed by partial or full structural collapse of zeolite having a silica/alumina molar ratio of 2 or less; and a hydrogen activation metal (M) cluster encapsulated in the aluminosilicate, wherein changes in hydrogen and carbon monoxide chemisorption amounts depending on the temperature satisfy the following relation:

$$0.7*(H/M_{373}+H/M_{473}+H/M_{573})/3 > (CO/M_{373}+CO/M_{473}+CO/M_{573})/3$$

wherein H/M is the chemisorption amount (mol) of a hydrogen atom per total mol of M, CO/M is the chemisorption amount (mol) of carbon monoxide per total mol of M, and subscripts represent adsorption temperatures (K).

In an exemplary embodiment, the catalyst shows the following:

$$0.8(MainP_{zeolite}) > (MainP_{collapse})$$

wherein $MainP_{zeolite}$ is the base area of the highest peak among XRD peaks of zeolite before collapse, and $MainP_{collapse}$ is the base area of an XRD peak at the same $2\theta$ of zeolite after collapse.

In an exemplary embodiment, the alumina/silica molar ratio of zeolite may be 1~2.

In an exemplary embodiment, the hydrogen activation metal may be any one or more selected from among Groups IB, VIIB and VIII metals on the periodic table, and specific examples thereof may include Co, Ni, Cu, Ru, Rh, Pd, Ag, Ir, Pt and/or Au.

In addition, a second aspect of the present invention provides a method of preparing a hydrogen spillover-based catalyst, including (a) providing zeolite containing a hydrogen activation metal (M) cluster therein and having a silica/alumina molar ratio of 2 or less; (b) ion-exchanging the zeolite with an ammonium ion ($NH_4^+$); and (c) thermally treating the ion-exchanged zeolite to thus partially or fully collapse a zeolite framework so that the hydrogen activation metal cluster is encapsulated in crystalline or amorphous aluminosilicate, wherein changes in hydrogen and carbon monoxide chemisorption amounts depending on the temperature satisfies the following relation:

$$0.7*(H/M_{373}+H/M_{473}+H/M_{573})/3 > (CO/M_{373}+CO/M_{473}+CO/M_{573})/3$$

wherein H/M is the chemisorption amount (mol) of a hydrogen atom per total mol of M, CO/M is the chemisorption amount (mol) of carbon monoxide per total mol of M, and subscripts represent adsorption temperatures (K).

In an exemplary embodiment, the zeolite may be P-type zeolite, A-type zeolite or X-type zeolite. Particularly useful is A-type zeolite.

In addition, a third aspect of the present invention provides a hydroprocessing/dehydrogenation method, including providing a hydrocarbon feed; and contacting the hydrocarbon feed with a hydrogen spillover-based catalyst in the presence of hydrogen.

As such, the hydrogen spillover-based catalyst includes crystalline or amorphous aluminosilicate formed by partial or full structural collapse of zeolite having a silica/alumina molar ratio of 2 or less; and a hydrogen activation metal (M) cluster encapsulated in the aluminosilicate, wherein changes in hydrogen and carbon monoxide chemisorption amounts depending on the temperature satisfy the following relation:

$$0.7*(H/M_{373}+H/M_{473}+H/M_{573})/3 > (CO/M_{373}+CO/M_{473}+CO/M_{573})/3$$

wherein H/M is the chemisorption amount (mol) of a hydrogen atom per total mol of M, CO/M is the chemisorption amount (mol) of carbon monoxide per total mol of M, and subscripts represent adsorption temperatures (K).

Advantageous Effects

According to embodiments of the present invention, a hydrogen spillover-based catalyst is configured such that a hydrogen activation metal cluster is encapsulated in crystalline or amorphous aluminosilicate formed by partial or full structural collapse of zeolite, and thus molecular hydrogen cannot diffuse into the catalyst at low temperature. Ultimately, active sites of hydrogen are separated from reactive sites with an organic material, thereby preventing a catalyst poison from being adsorbed to the surface of metal and exhibiting reaction properties different from conventional metal-supported catalysts reacting on the surface of metal, that is, high catalytic activity (hydrogenation, hydrodeoxygenation, hydrodenitrogenation, hydrodesulfurization, hydroisomerization, dehydrogenation, etc.) and low C—C hydrogenolysis activity (by about 70% or less compared to the hydrogenolysis activity of a conventional $Pt/SiO_2$ catalyst obtained by wet impregnation). Also, the hydrogen activation metal is encapsulated in structurally stable aluminosilicate, thereby preventing sintering of the metal, consequently ensuring superior thermal stability.

BEST MODE

Figures 1, 2:
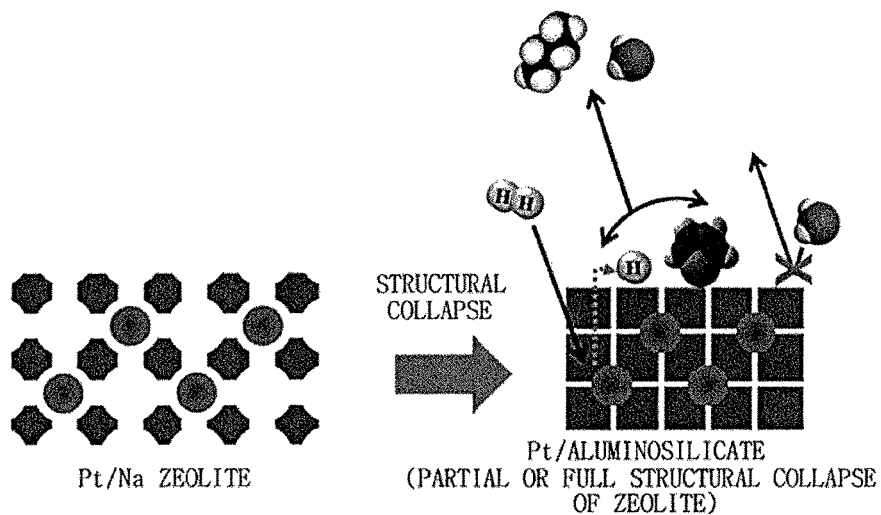
FIG. 1 schematically illustrates a hydrogen spillover mechanism occurring in a catalyst configured such that a hydrogen activation metal cluster is encapsulated (supported) in crystalline or amorphous aluminosilicate formed by structural collapse of zeolite, according to an embodiment of the present invention.
FIG. 2 illustrates the results of measurement of physical/chemical properties of samples (Pt/NaA-0, Pt/NaA-0.24 and Pt/NaA-0.95) in which Pt is selectively encapsulated (supported) in NaA zeolites having various BET areas, samples (Pt/NaHA-0, Pt/NaHA-0.24 and Pt/NaHA-0.95) in which a Pt cluster is encapsulated (supported) in aluminosilicate formed by partial structural collapse of NaA zeolite, samples (Pt/HA-0, Pt/HA-0.24 and Pt/HA-0.95) in which a Pt cluster is encapsulated (supported) in aluminosilicate formed by full structural collapse of NaA zeolite, and a common $Pt/SiO_2$ sample prepared by an conventional wet impregnation process, in Example 1.

The present invention may be accomplished by the following description. The following description is to be understood to disclose embodiments of the present invention, and the present invention is not necessarily limited thereto. Also, the appended drawings are used to aid understanding of the present invention, and the present invention is not limited thereto, and details on individual components may be properly understood by the specific purpose of the relevant description below.

The terms used herein may be defined as follows.

The term "hydrogen activation metal" broadly refers to a metal able to form activated hydrogen, that is, dissociated hydrogen, by contact with molecular hydrogen.

The term "hydrogen spillover" refers to diffusion of dissociated hydrogen (i.e. activated hydrogen atoms) from a hydrogen-rich metal cluster, where hydrogen atoms are produced through dissociation of molecular hydrogen, to the surface of a support where hydrogen dissociation is improbable.

The term "hydroprocessing" refers to any catalytic process using hydrogen, and typically includes reaction of a hydrocarbon distillate with hydrogen in the presence of a catalyst. Examples thereof may include hydrogenation, hydrodesulfurization, hydrodenitrogenation, hydrodewaxing (hydroisomerization), hydrodeoxygenation, etc.

The term "hydrogenation" refers to a reaction for increasing hydrogen content in a hydrocarbon compound by chemically adding hydrogen to at least a portion of the hydrocarbon compound through contact of the hydrocarbon compound with a catalyst in the presence of hydrogen, and typically includes saturation reactions such as olefin hydrogenation and aromatic hydrogenation.

The term "hydrodewaxing" broadly refers to a reaction for removing a wax component (especially n-paraffin) from a hydrocarbon distillate in the presence of hydrogen, and narrowly refers to a reaction for typically converting n-paraffin into iso-paraffin as "hydroisomerization."

The term "hydrodesulfurization" refers to a process for removing a sulfur component from a hydrocarbon distillate in the presence of hydrogen supply.

The term "hydrodenitrogenation" refers to a process for removing a nitrogen component from a hydrocarbon distillate in the presence of hydrogen supply.

The term "hydrodeoxygenation" refers to a reaction for removing oxygen in the form of water from a compound in the presence of hydrogen supply.

The term "dehydrogenation" refers to a reaction for removing hydrogen from a compound.

The term "C—C hydrogenolysis" refers to cleavage of a single bond between carbon and carbon by hydrogen.

According to an embodiment of the present invention, a hydrogen spillover-based catalyst is configured such that a hydrogen activation metal (M) cluster is encapsulated in aluminosilicate to which partial or full (or entire) zeolite structure is collapsed.

In the present invention, the chemisorption amount of each of hydrogen ($H_2$) and carbon monoxide (CO) may be measured by a volumetric method known in the art. This is because an increase in hydrogen chemisorption amount depending on the temperature in a structurally collapsed material such as the catalyst according to the present embodiment may be accurately measured by a volumetric method. In the case where the hydrogen chemisorption amount is measured by a pulse method as a method other than the volumetric method, limitations are imposed on actually observing the increase in the hydrogen chemisorption amount depending on the temperature. This is considered to be due to insufficient equilibrium time in the pulse method. Specifically, because the rate of diffusion of hydrogen into the catalyst even at high temperature is not sufficiently high, the measurement method for allowing hydrogen to flow in the form of pulse in the catalyst, such as the pulse method, makes it difficult to ascertain the increase in chemisorption amount.

In the present embodiment, upon measurement of hydrogen ($H_2$) and carbon monoxide (CO) chemisorption amounts, as the adsorption temperature rises, $H_2$ shows a tendency to increase the adsorption amount. Specifically, hydrogen and carbon monoxide chemisorption properties depending on the temperature are as follows:

$$0.7*(H/M_{373}+H/M_{473}+H/M_{573})/3 > (CO/M_{373}+CO/M_{473}+CO/M_{573})/3$$

wherein H/M is the chemisorption amount (mol) of a hydrogen atom per total mol of M, CO/M is the chemisorption amount (mol) of carbon monoxide per total mol of M, and subscripts represent the adsorption temperatures (K).

In a typical hydrogenation catalyst having externally exposed metal and a catalyst configured such that a metal is encapsulated in zeolite the structure of which is not collapsed (where hydrogen is accessible to the surface of metal at room temperature), kinetic energy of an adsorption molecule is increased in proportion to a rise in the adsorption temperature, thus lowering the chemisorption amount. The reason why the catalyst according to the present embodiment shows hydrogen adsorption properties different from typically expected catalytic behavior is that molecular hydrogen is difficult to diffuse into structurally collapsed aluminosilicate at low temperature (less than 323 K) but may diffuse into the catalyst depending on the temperature rise. In the case of carbon monoxide, even when the temperature rises, the adsorption amount is not increased, and thus hydrogen and carbon monoxide chemisorption properties as above are exhibited.

FIG. 1 schematically illustrates a hydrogen spillover mechanism in a catalyst configured such that a hydrogen activation metal cluster is encapsulated (supported) in aluminosilicate formed by structural collapse of zeolite.

As illustrated in this drawing, the hydrogen activation metal (e.g. Pt) is encapsulated in aluminosilicate formed by structural collapse of zeolite (e.g. A-type zeolite or X-type zeolite). As such, because aluminosilicate has micropores (e.g. fully collapsed aluminosilicate has a diameter of less than about 0.29 nm at room temperature), a very simple catalyst poison component such as hydrogen sulfide ($H_2S$) as well as an organic sulfur compound (e.g. thiophene) cannot diffuse (inaccessible) to the surface of metal. In particular, it is difficult for molecular hydrogen to diffuse to the surface of metal in aluminosilicate at low temperature.

However, as molecular hydrogen selectively diffuses to the surface of metal in the catalyst depending on the temperature rise (the hydrogen chemisorption amount increases), the molecular hydrogen is dissociated by the metal, thereby producing activated hydrogen. The activated hydrogen is moved to the surface of the catalyst through the micropores of aluminosilicate and thus reacts with an organic molecule (in the drawing, an organic sulfur compound, etc.) which is present on the surface, producing hydrocarbon and hydrogen sulfide.

Unlike the spillover principle in the hydrogenation as illustrated in FIG. 1, hydrogen is removed from the organic molecule upon dehydrogenation. In this case, a reverse spillover phenomenon occurs (specifically, hydrogen atoms produced by dehydrogenation of cycloalkane such as cyclohexane diffuse to the surface of metal through micropores of aluminosilicate, and are recombined to produce molecular hydrogen).

The catalyst according to the embodiment of the present invention exhibits superior hydroprocessing and dehydrogenation activities, compared to a metal-containing catalyst having a large crystal size and an unchanged zeolite structure. Although the present invention is not confined to a specific theory, such activity improvements may be elucidated by rapid diffusion of molecular hydrogen to the surface of metal in the catalyst because of decrease in thickness of the framework and in a length of a diffusion pathway in the aluminosilicate matrix, more rapid movement of activated hydrogen to the surface of aluminosilicate, or an increase in the number of active sites on the surface of the aluminosilicate matrix where spillover hydrogen is added (hydrogenation) or is removed (dehydrogenation) from the reactant molecule.

According to an embodiment, zeolite may be partially or fully structurally collapsed by subjecting zolite having high Al content to subsequent ion exchange and thermal treatment. The silica/alumina molar ratio (SAR) of zeolite before collapse may be about 2 or less and more particularly may be in the range of about 1~2. When using zeolite having a comparatively low SAR (zeolite having high Al content), the crystal structure thereof may be collapsed by subsequent ion exchange and thermal treatment. In this regard, SAR of zeolite before collapse becomes substantially equal to that of crystalline or amorphous aluminosilicate after collapse (partial or full collapse).

In an embodiment, the metal encapsulated in structurally collapsed zeolite is a hydrogen activation metal and is not limited to specific species, but may include any one or more selected from among Groups IB, VIIB and VIII on the periodic table. More specifically, a typical hydrogen activation metal may be Co, Ni, Cu, Ru, Rh, Pd, Ag, Ir, Pt and/or Au. The hydrogen activation metal is encapsulated in the aluminosilicate matrix and thus dispersed in the form of a cluster, and the diameter of the metal cluster may be for example about 0.5~50 nm, particularly about 0.5~10 nm, and more particularly about 0.5~2 nm. Also, the amount of the hydrogen activation metal in the catalyst may be for example about 0.01~10 wt %, particularly about 0.1~2 wt %, and more particularly about 0.5~1.5 wt %, based on the weight of the catalyst.

Also, the BET specific surface area of the catalyst shows a tendency to decrease in proportion to an increase in the degree of collapse of zeolite. As such, the typical specific surface area of partially or fully structurally collapsed zeolite (i.e. crystalline or amorphous aluminosilicate) may be for example about 1~800 m²/g, particularly about 2~200 m²/g, and more particularly about 2~60 m²/g.

In an exemplary embodiment, the alkali metal/Al molar ratio in the catalyst may be for example about 0.9 or less, particularly about 0.01~0.8, and more particularly about 0.05~0.6 (alkali metal used upon preparation of zeolite, or the case where alkali metal ion-containing zeolite is ion-exchanged with another alkali metal and then with an ammonium ion to thereby collapse the structure thereof, as will be described later). In an alternative embodiment, the alkaline earth metal/Al molar ratio in the catalyst may be for example about 0.45 or less, particularly about 0.005~0.4, and more particularly about 0.025~0.3 (the case where alkali metal ion-containing zeolite is ion-exchanged with an alkaline earth metal and then with an ammonium ion to thereby collapse the structure thereof, as will be described later).

When partially or fully structurally collapsing the zeolite, XRD (X-ray Diffraction) peaks decrease, and specifically the following properties are shown:

$$0.8(\text{MainP}_{zeolite}) > (\text{MainP}_{collapse})$$

wherein $\text{MainP}_{zeolite}$ is the base area of the highest peak among XRD peaks of zeolite before collapse, and $\text{MainP}_{collapse}$ is the base area of the XRD peak at the same 2θ of zeolite after collapse.

Meanwhile, the catalyst has a low hydrogen chemisorption amount to the extent that molecular hydrogen is inaccessible to the metal encapsulated in aluminosilicate at low temperature. The exemplary chemisorption ranges (at different temperatures) are given in Tables 1 and 2 below.

TABLE 1

Hydrogen chemisorption ranges at different temperatures upon partial and full structural collapse

| Temp. (K) | Comprehensive range (H/M) | Specific range (H/M) |
|---|---|---|
| 323 | 0~0.3 | 0~0.15 |
| 373 | 0.005~0.5 | 0.01~0.3 |
| 473 | 0.02~0.5 | 0.03~0.3 |
| 573 | 0.05~0.5 | 0.08~0.3 |

TABLE 2

Hydrogen chemisorption ranges at different temperatures upon full structural collapse

| Temp. (K) | Comprehensive range (H/M) | Specific range (H/M) |
|---|---|---|
| 323 | 0~0.1 | 0~0.05 |
| 373 | 0~0.2 | 0~0.15 |
| 473 | 0.01~0.2 | 0.05~0.15 |
| 573 | 0.02~0.2 | 0.08~0.15 |

In an exemplary embodiment, the catalyst configured such that a hydrogen activation metal is encapsulated in aluminosilicate which is structurally collapsed zeolite may be additionally ion-exchanged with a variety of cations, and examples of such cations may include metal ions of Groups IA, IIA, IIIB, VII, IB, VIII, etc. on the periodic table.

In an exemplary embodiment of the present invention, a binder known in the art to improve physical/mechanical properties or to perform a forming process may be used together with the above catalyst. Examples of the binder may include clay, inorganic oxide, etc., and the inorganic oxide is particularly exemplified by silica, alumina, silica-alumina, silica-magnesia, silica-zirconia, silica-thoria, silica-titania, etc. The binder may be used in an amount of about 10~90 wt %, and particularly about 30~70 wt % based on the amount of the catalyst, but the present invention is not necessarily limited thereto.

Preparation of Catalyst

According to another embodiment of the present invention, a method of preparing a hydrogen spillover-based catalyst includes preparation of metal-containing zeolite, ion-exchange and thermal treatment in order.

Preparation of Metal-Containing Zeolite

In an embodiment, zeolite is prepared from a mixture comprising water, a silica source, an alumina source, and a mineralizer ($OH^-$, $F^-$, etc.) using, for example, a hydrothermal synthesis process. Zeolite thus prepared is zeolite having high Al content (aluminous zeolite), and is typically exemplified by P-type zeolite, A-type zeolite, X-type zeolite, etc.

Examples of the silica source may include silicate, silica gel, colloidal silica, fumed silica, tetralkyl orthosilicate, silica hydroxide, precipitated silica, clay, etc. Among the above-listed examples of the silica source, precipitated silica and silica gel are commercially available under the brand name of Zeosil, and colloidal silica is commercially available under the brand name of Ludox.

In the case of the alumina source, it may be present in the form of an alumina soluble salt, and examples thereof may include a sodium salt, chloride, aluminum alcoholate, hydrated alumina (e.g. gamma-alumina), pseudoboehmite and colloidal alumina.

In an exemplary embodiment, the reaction mixture for zeolite synthesis may have the following composition (represented by oxides) (molar ratio):
$SiO_2/Al_2O_3$: about 1~20,
$H_2O/M'_2O$: about 10~120,
$M'_2O/SiO_2$: about 0.38~3, and
$OH^-/SiO_2$: about 0.76~6,
wherein M' indicates the alkali metal.

Particularly in an exemplary embodiment, the reaction mixture for A-type zeolite synthesis may have the following composition (molar ratio):
$SiO_2/Al_2O_3$: about 1~2.5,
$H_2O/M'_2O$: about 40~120,
$M'_2O/SiO_2$: about 0.8~3, and
$OH^-/SiO_2$: about 1.6~6,
wherein M' indicates the alkali metal.

In the above embodiment, to prepare a desired type of zeolite (e.g. P-type zeolite, A-type zeolite or X-type zeolite), the specific material composition and synthesis temperature (hydrothermal synthesis temperature) may be set in the above material composition range. The basic contents for the reaction material composition and the synthesis temperature depending on the type of zeolite are described in, for example, W. Breck, Zeolite Molecular Sieves, Wiley, New York, p 271, 1974, which is incorporated herein by reference into the present application. As such, the hydrogen activation metal may be added in the form of a precursor known in the art to the reaction mixture for zeolite synthesis. It is noted that, even when zeolite is synthesized in the above material composition range, the silica/alumina molar ratio (SAR) of (as-synthesized) zeolite before collapse needs to be about 2 or less in order to achieve structural collapse of zeolite as will be described later.

In a specific embodiment of the present invention, a crystal growth inhibitor, for example, polyethyleneglycol (PEG) may be added to the reaction mixture to control the specific surface area and the crystal size of synthesized zeolite, and may be added at a molar ratio of for example about up to 2, particularly about 0.1~1.5, and more particularly about 0.2~1 relative to the amount of alumina ($Al_2O_3$; when represented by an oxide) in the reaction mixture. Furthermore, organosilane may be used as the crystal growth inhibitor, and may be added at a molar ratio of for example about 0.0001~0.5, particularly about 0.0005~0.2, and more particularly about 0.001~0.1 relative to the amount of silicon oxide ($SiO_2$; when represented by an oxide) in the reaction mixture. As such, the organosilane may be represented by Chemical Formula 1 below:

 [Chemical Formula 1]

wherein a is an integer of 1~3, X is a hydrolysable group upon synthesis, for example, a hydroxyl group, a halide group or an alkoxy group, and R is an alkyl group or an alkenyl group.

As such, the alkyl group may be in the form of being substituted with a hydroxyl group, a halide group, a thiol group, an amino group, a cyano group, a nitro group, an amide group, a carboxylic acid group or a sulfonic acid group.

Typical examples of the organosilane may include the following and may be used alone or in combinations, but the present invention is not limited thereto:
[3-(trimethoxysilyepropyl]octadecyldimethylammonium chloride; [3-(trimethoxysilyl)propyl]hexadecyldimethylammonium chloride; [3-(trimethoxysilyl)propyl]dodecyldimethylammonium chloride; [3-(trimethoxysilyl)propyl]octylammonium chloride; N-[3-(trimethoxysilyl)propyl]aniline; 3-[2-(2-aminoethylamino)ethylamino]propyl-trimethoxdysilane; N-[3-(trimethoxysilyl)propyl]ethylenediamine; triethoxy-3-(2-imidazolin-1-yl)propylsilane; 1-[3-(trimethoxysilyl)propyl]urea; N-[3-(trimethoxysilyl)propyl]ethylenediamine; [3-(diethylamino)propyl]trimethoxysilane; (3-glycidyloxypropyl)trimethoxysilane; 3-(trimethoxysilyl)propyl methacrylate; [2-(cyclohexenyl)ethyl]triethoxysilane; dodecyltriethoxysilane; hexadecyltrimethoxysilane; (3-aminopropyl)trimethoxysilane; (3-mercaptopropyl)trimethoxysilane; and (3-chloropropyl)trimethoxysilane.

As the amount of added PEG and/or organosilane increases, the crystal size decreases but the specific surface area increases. Illustratively, the crystal size of synthesized zeolite may be for example about 20~3000 nm, particularly about 30~1800 nm, and more particularly about 60~1800 nm.

In an embodiment, the hydrogen activation metal is incorporated in zeolite to thus prepare metal-containing zeolite. In this regard, encapsulation of a metal cluster in zeolite may protect active sites and may improve reaction efficiency depending on the selection of reactants, products or transition state, and various methods therefor may be taken into consideration. In an exemplary embodiment, because the case where the metal cluster is stably encapsulated in the aluminosilicate matrix even after structural collapse of zeolite is desirable, the hydrogen activation metal may be selectively incorporated in the form of a cluster having a uniform size in zeolite during preparation of metal-containing zeolite. However, in conventional cases, metal hydroxide may precipitate in the course of increasing pH during synthesis of zeolite. In an exemplary embodiment, zeolite is prepared in such a manner that mercaptosilane is added together with a hydrogen activation metal (M) precursor to the reaction mixture, thereby solving the above problems. In this case, mercaptosilane may be added at a molar ratio of for example about 0.01~0.5, particularly about 0.03~0.2, and more particularly about 0.05~0.1 relative to alumina ($Al_2O_3$; when represented by an oxide) in the reaction mixture. The mercapto group (—SH) of silane inhibits formation of metal hydroxide in an alkali medium necessary for zeolite synthesis, and an alkoxysilane moiety is hydrolyzed and condensed with a zeolite precursor. As a result, Si—O—Si or Si—O—Al bonding is formed to thus induce crystallization of an inorganic framework around the metal-organosilane complex. Like this, the hydrogen activation metal may be selectively effectively encapsulated in zeolite because of bifunctionality of the organosilane ligand. Examples of mercaptosilane may include mercaptopropyltrimethoxysilane, mercaptopropyltriethoxysilane, etc. Such mercaptosilane may be removed in the course of drying and thermal treatment which are typically performed upon zeolite synthesis. As such, thermal treatment may be carried out at for example about 573~773 K (particularly, about 600~700 K) for about 1~3 hr (particularly, 1.5~2.5 hr) in an oxygen (air) and/or hydrogen atmosphere and/or inert atmosphere. These thermal treatment conditions may be illustratively understood, and the present invention is not limited thereto.

On the other hand, in an alternative embodiment, as-synthesized or commercially available zeolite (e.g. alkali metal ion-containing zeolite such as Na-zeolite) is impregnated (especially wet-impregnated) or ion-exchanged with a hydrogen activation metal (M) precursor, and then thermally treated, so that the hydrogen activation metal (M) may be selectively incorporated in the form of a cluster having a uniform size in zeolite. Furthermore, impregnated or ion-exchanged zeolite may be selectively dried before thermal treatment. As the hydrogen activation metal precursor, any salt or complex of the corresponding metal known in the art may be used without particular limitation so long as zeolite is impregnated or ion-exchanged therewith. For instance, in the case where Pt is used as the hydrogen activation metal, hydrides, fluorides (e.g. $PtF_6$, $PtF_4$, $[PtF_5]_4$, etc.), chlorides (e.g. $PtCl_3$, $PtCl_4$, $Pt_6Cl_{12}$, etc.), bromides ($PtBr_3$, $PtBr_4$, etc.), iodides (e.g. $PtI_2$, $PtI_3$, $PtI_4$, etc.), oxides (e.g. $PtO$, $PtO_2$, $PtO$, etc.), sulfides (e.g. $PtS$, $PtS_2$, etc.), carbonyls (e.g. $Pt(CO)_4$) and/or complexes (e.g. $[PtCl_2(NH_3)_2]$, $[PtCl_2(NH_3)_2]$, $K_2[PtCl_6]$, $K_2[Pt(CN)_4]$, $PtCl_4 \cdot 5H_2O$, $K[PtCl_3(NH_3)]$, $Na_2[PtBr_6] \cdot 6H_2O$, $(NH_4)_2[PtBr_6]$, $K_2[PtI_6]$, $(NH_4)_2[PtCl_6]$, $K_2[Pt(CN)_6]$, $(NH_4)_2[PtCl_4]$, $K_2[Pt(NO_2)_4]$, $K[PtCl_3(C_2H_4)] \cdot H_2O[Pt(NH_3)_4](NO_3)_2$, $H_2PtCl_6$, etc.) may be used, but the present invention is not limited thereto. Also, the hydrogen activation metal precursor for wet impregnation or ion exchange may be used in the form of an aqueous solution and/or an organic solution. Examples of the organic solvent may include, but are not necessarily limited to, acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethyl ether, diethylene glycol, diglyme (diethylene glycol dimethyl ether), 1,2-dimethoxy-ethane (glyme; DME), dimethylether, dimethyl-formamide (DMF), dimethyl sulfoxide (DMSO), dioxane, ethanol, ethyl acetate, ethylene glycol, glycerin, heptanes, hexamethylphosphoramide (HMPA), hexamethylphosphoroustriamide (HMPT), hexane, methanol, methyl t-butyl ether (MTBE), methylene chloride, N-methyl-2-pyrrolidinone (NMP), nitromethane, pentane, 1-propanol, 2-propanol, pyridine, tetrahydrofuran (THF), toluene, triethyl amine, o-xylene, m-xylene, p-xylene, etc.

In an exemplary embodiment, of the incorporation process, an ion exchange process using a metal hydride salt (or complex) aqueous solution may be performed at 283~363 K (particularly about 293~333 K, and more particularly about 297~313 K) for about 1~24 hr (particularly, 2~12 hr, and more particularly 4~6 hr), and the metal hydride salt aqueous solution may have a concentration of 0.000001~1 M (particularly 0.0001~0.1 M, and more particularly 0.0005~0.01 M), but is not necessarily limited thereto.

Also, thermal treatment may be conducted at for example about 500~800 K (particularly about 573~773 K, and more particularly about 600~700 K) for about 1~3 hr (particularly, 1.5~2.5 hr) in an oxygen (air) and/or hydrogen atmosphere and/or inert atmosphere. These thermal treatment conditions may be illustratively understood, but are not necessarily limited thereto.

The incorporation process of the hydrogen activation metal as above may be more effectively applied to X-type zeolite having a comparatively large pore size.

In the case of synthesized zeolite having the hydrogen activation metal cluster encapsulated therein as above, optional substitution of the alkali metal ion (e.g. $Na^+$) in synthesized zeolite (i.e. zeolite extraframework) with another alkali metal (e.g. $Li^+$ and $K^+$), alkaline earth metal (e.g. $Mg^{2+}$ and $Ca^{2+}$), etc. may control structural and chemical properties of zeolite. As such, zeolite having an alkali metal (e.g. alkali metal ion-exchanged with $Na^+$, other than $Na^+$) or an alkaline earth metal (e.g. alkaline earth metal ion-exchanged with $Na^+$) may be ion-exchanged with an ammonium ion, etc. as illustrated in Scheme 1 below.

[Scheme 1]

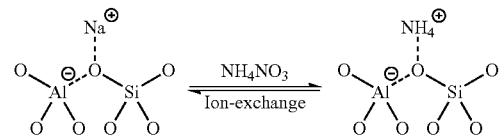

As such, the amount of ion exchange may be determined in a range able to at least partially collapse the zeolite crystal structure by subsequent thermal treatment. In a specific embodiment, in the case where the amount of ion exchange is adjusted so that zeolite is partially structurally collapsed upon subsequent thermal treatment, more favorable reaction activity may be obtained. This is because the optimal value between the gas diffusion rate of hydrogen in the aluminosilicate matrix and the surface diffusion rate of activated hydrogen may be deduced through partial collapse.

In this regard, in the case where the alkali metal in zeolite is ion-exchanged with another alkali metal or an alkaline earth metal and then with an ammonium ion, the degree (i.e. the molar ratio to Al) of ion exchange in zeolite may be represented by General Formula 1 below:

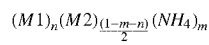   [General Formula 1]

wherein M1 and M2 are an alkali metal and an alkaline earth metal, respectively, m may be adjusted in the range of $0.1 \leq m \leq 1$, and the degree of ion exchange of the alkali metal and alkaline earth metal may be adjusted in the range of $0 \leq n \leq 1-m$.

In an exemplary embodiment, m and n in General Formula 1 may be adjusted in the range in which the $NH_4^+/Al$ molar ratio is about 0.1~1.

Typically, an ion exchange reaction is performed by contacting zeolite with a solution having a desired exchange ion salt. Details of the typical ion exchange reaction are disclosed in a variety of literature including U.S. Pat. Nos. 3,140,249, 3,140,251, etc., which are incorporated herein by reference into the present application. In the present embodiment, the cation (alkali metal or alkaline earth metal cation) of the synthesized metal-containing zeolite extraframework is ion-exchanged with an ammonium ion. In a specific embodiment, the ammonium ion-containing compound used for ion exchange may include ammonium nitrate, ammonium chloride, ammonium sulfate, etc. and ion exchange may be performed once or more than two times to achieve the desired degree of ion exchange. Typically, the metal-containing zeolite may be ion-exchanged by a contact process with an ammonium ion-containing compound aqueous solution (having a concentration of about 0.005~1M) at about 20~80° C. for about 1~24 hr (particularly, about 5~10 hr).

The metal-containing zeolite thus ion-exchanged is partially or fully collapsed by subsequent thermal treatment. As such, the degree of structural collapse depends on the amount of ion exchange with an ammonium ion. In an embodiment, the ion-exchanged metal-containing zeolite is decationized by thermal treatment at about 373~973 K and particularly about 473~773 K in an oxygen atmosphere (e.g. air) and/or a hydrogen atmosphere and/or an inert atmosphere, and ultimately the collapse of the zeolite crystal structure is induced.

The ammonium ion-exchanged zeolite (with high Al content) is present in an unstable state, and thus the crystal structure thereof may be collapsed even by only thermal treatment at a temperature less than 423 K which is comparatively low. Also, aluminosilicate which is partially or fully structurally collapsed zeolite is decreased in specific surface area compared to zeolite before thermal treatment, and shows a microporous structure. As such, the metal cluster incorporated in zeolite is dispersed in the form of being encapsulated in the crystalline or amorphous aluminosilicate matrix after structural collapse.

Compared to a conventionally known common catalyst or a catalyst having a metal cluster incorporated (encapsulated) in an unchanged zeolite structure, the catalyst configured such that the metal particles are encapsulated in aluminosilicate which is partially or fully structurally collapsed zeolite enables diffusion of hydrogen (at an increased temperature) but makes it impossible to achieve access of the organic molecule to the metal cluster in the catalyst, and thus it may act as a hydrogen spillover-based catalyst.

According to another embodiment of the present invention, in the case where the catalyst configured such that the metal cluster is encapsulated in aluminosilicate which is partially or fully structurally collapsed zeolite is applied to various hydroprocessing and dehydrogenation processes, an improved activity is manifested. Examples of the hydroprocessing include hydrogenation, hydrodesulfurization, hydrodenitrogenation, hydrodeoxygenation, hydroisomerization, etc. A typical example of dehydrogenation may include conversion of cyclohexane into benzene. Furthermore, it may be utilized in an oxygen reduction reaction to prepare hydrogen peroxide.

The catalyst according to the present embodiment may exhibit a significantly low level for C—C hydrogenolysis. In some cases, it is noted that it does not substantially show C—C hydrogenolysis activity. Typically, in the case of hydrogenolysis, the catalytic activity is known to depend on the size of the metal cluster. Briefly, the smaller the size of the metal cluster, the higher the activity. However, the catalyst according to the present embodiment suppresses C—C hydrogenolysis activity despite the microsized metal cluster being incorporated (dispersed) in the aluminosilicate matrix. The reason why the activity as opposed to the prior known results is shown is that the active sites of the surface of the catalyst reacting with the spillover hydrogen cannot cleave C—C bonds of the organic molecule. Such reaction properties are advantageous because loss of the hydrocarbon reactants into light hydrocarbon gases having low value upon hydroprocessing may be effectively suppressed.

Moreover, even when the catalyst according to the present embodiment, in which the hydrogen activation metal cluster is encapsulated in structurally stable aluminosilicate, is applied to severe high-temperature conditions, sintering of the metal may be more effectively suppressed, thereby exhibiting superior heat resistance, compared to a typical hydroprocessing or dehydrogenation catalyst wherein the metal is exposed to the surface of a support. A better understanding of the present invention may be obtained via the following examples which are set forth to illustrate, but are not to be construed as limiting the present invention.

EXAMPLE 1

Selective Incorporation of Pt into NaA Zeolites Having Various BET Surface Areas Sodium aluminate ($Na_2O$ 42.5%, $Al_2O_3$ 53%, Aldrich) and Ludox (AS-30, 30 wt % in $H_2O$, Aldrich) were used as an alumina source and a silica source, respectively. To synthesize zeolites having various BET surface areas, a reaction mixture (a gel composition) was added with polyethyleneglycol (PEG, Average Mn; 1450, Aldrich) at a ratio of 0 wt %, 50 wt % and 200 wt % relative to water respectively. Then, mercaptopropyltrimethoxysilane and as a Pt precursor platinic acid ($H_2PtCl_6$) were added together to the reaction mixture. Consequently, the final composition of the reaction mixture was as follows (based on mol):

($1.5SiO_2$:$Al_2O_3$:$1.8Na_2O$:$38.12H_2O$:$0.016Pt$:$0.064$mercaptosilane:nPEG (n is 0~0.95)).

The sufficiently mixed reaction mixture was stirred at 353 K for 18 hr, after which a solid product was obtained by filtration, and then dried at 373 K for 24 hr, affording zeolite (NaA zeolite). Thereafter, such zeolite was thermally treated at 673 K for 2 hr in each of an air atmosphere and an $H_2$ atmosphere.

As for samples in which Pt was supported in synthesized NaA zeolite, the BET surface area was measured at 77 K using nitrogen adsorption. Nitrogen adsorption was measured using a BEL-Sorp-max system (BEL Japan). Before measurement of the adsorption, all the samples were pretreated at 673 K in a vacuum, and the surface area of the samples was calculated by an equation of Brunauer-Emmett-Teller (BET) under the condition that the relative pressure ($P/P_0$) was in the range of 0.05~0.20. Ultimately, Pt-supported NaA zeolites having BET surface areas of 3 $m^2$ $g^{-1}$, 18 $m^2$ $g^{-1}$ and 38 $M^2$ $g^{-1}$ could be synthesized.

The amount of Pt supported in synthesized NaA-zeolite was analyzed by inductively coupled plasma atomic emission spectroscopy (ICP-AES) using iCAP-6500 (Thermo elemental), and the mol number of Pt exposed to the surface was analyzed by measuring $H_2$ and CO chemisorption amounts using ASAP2000 (Micromeretics) at 323 K (a volumetric vacuum method). $H_2$ (99.999%) and CO (99.9%) gases were used without additional purification. Before analysis of the adsorption, all the samples were reduced for 1 hr while allowing $H_2$ to flow at 673 K (100 sccm), and then subjected to vacuum treatment at the same temperature for 1 hr. The chemisorption of hydrogen and carbon monoxide was measured by a volumetric method using ASAP2020 (Micromeritics), and the chemisorption amounts thereof were measured at 323 K, 373 K, 473 K and 573 K after reduction at 673 K for 1 hr. Specifically, the samples were pretreated through the following procedures:

(i) While allowing hydrogen to flow at 100 ml/min, the sample was heated to 373 K at 10 K/min and maintained for 30 min;

(ii) While allowing hydrogen to flow at 100 ml/min, the sample was heated to 673 K at 10 K/min and maintained for 60 min;

(iii) The sample was maintained at 673 K for 60 min in a vacuum;

(iv) The sample was cooled to adsorption temperature (323 K, 373 K, 473 K, 573 K) at 50 K/min in a vacuum and maintained for 60 min; and (v) A leak test was performed so that "outgas rate" was 10 μm/min or less at adsorption temperature (323 K, 373 K, 473 K, 573 K).

Specific measurement of the chemisorption amount was performed under the following conditions:
Equilibration interval: 20 sec
Relative target tolerance: 5.0%
Absolute target tolerance: 5.000 mmHg
Measuring pressure: 2~450 mmHg.

By extrapolation of the high pressure (50~200 mmHg) zone of the adsorption isotherm obtained under the above conditions, the hydrogen and carbon monoxide chemisorption amounts at the corresponding adsorption temperature were determined. As such, the equilibration interval of 20 sec means that equilibration of the chemisorption amount is checked at an interval of 20 sec, and the relative target tolerance means that the case where a change in the chemisorption amount is less than 5% for the corresponding equilibration interval becomes equilibrium. Also, the absolute target tolerance means that the case where the absolute absorption amount is less than 5 mmHg becomes equilibrium. The case where both the relative and the absolute tolerance are satisfied is determined to be adsorption.

The properties of the synthesized materials are summarized in FIG. 2. Depending on the mol composition of PEG added upon synthesis of NaA zeolite, the samples were denoted as Pt/NaA-0, Pt/NaA-0.24 and Pt/NaA-0.95.

Separately, mesoporous silica gel (Davisil Grade 636, Sigma-Aldrich) was initially wet-impregnated with a $Pt(NH_3)_4(NO_3)_2$ (Aldrich) aqueous solution. The impregnated silica gel was dried at 373 K for 24 hr, calcined at 673 K for 2 hr in dry air (200 ml $min^{-1}$ $g^{-1}$), and reduced at 773 K for 2 hr in a hydrogen atmosphere (200 ml $min^{-1}$ $g^{-1}$), thereby preparing a $Pt/SiO_2$ catalyst sample. The properties of the $Pt/SiO_2$ catalyst sample are shown in FIG. 2.

Structural Collapse of Zeolite by $NH_4^+$ Ion Exchange and Thermal Treatment

Each NaA zeolite synthesized by the above procedures was ion-exchanged over 6 hr at room temperature using a 0.5 M ammonium nitrate ($NH_4NO_3$) solution. Some of synthesized Pt-supported NaA zeolites were ion-exchanged once using 14 ml of a 0.5 M ammonium nitrate ($NH_4NO_3$) solution per 1 g, and the others were ion-exchanged three times using 140 ml of a 0.5 M ammonium nitrate ($NH_4NO_3$) solution per 1 g. The ion-exchanged samples were thermally treated at 673 K in an air atmosphere, and the degree of collapse of the zeolite crystal structure was analyzed by XRD. As such, the samples, which were ion-exchanged once with the ammonium nitrate solution, were denoted as Pt/NaHA-0, Pt/NaHA-0.24 and Pt/NaHA-0.95 (partial collapse), depending on the mol amount of PEG added in the course of synthesis of NaA zeolite. Also, the samples, which were ion-exchanged three times, were denoted as Pt/HA-0, Pt/HA-0.24 and Pt/HA-0.95 (full collapse), depending on the mol amount of PEG added in the course of synthesis of NaA zeolite.

XRD Analysis

Figure 3:
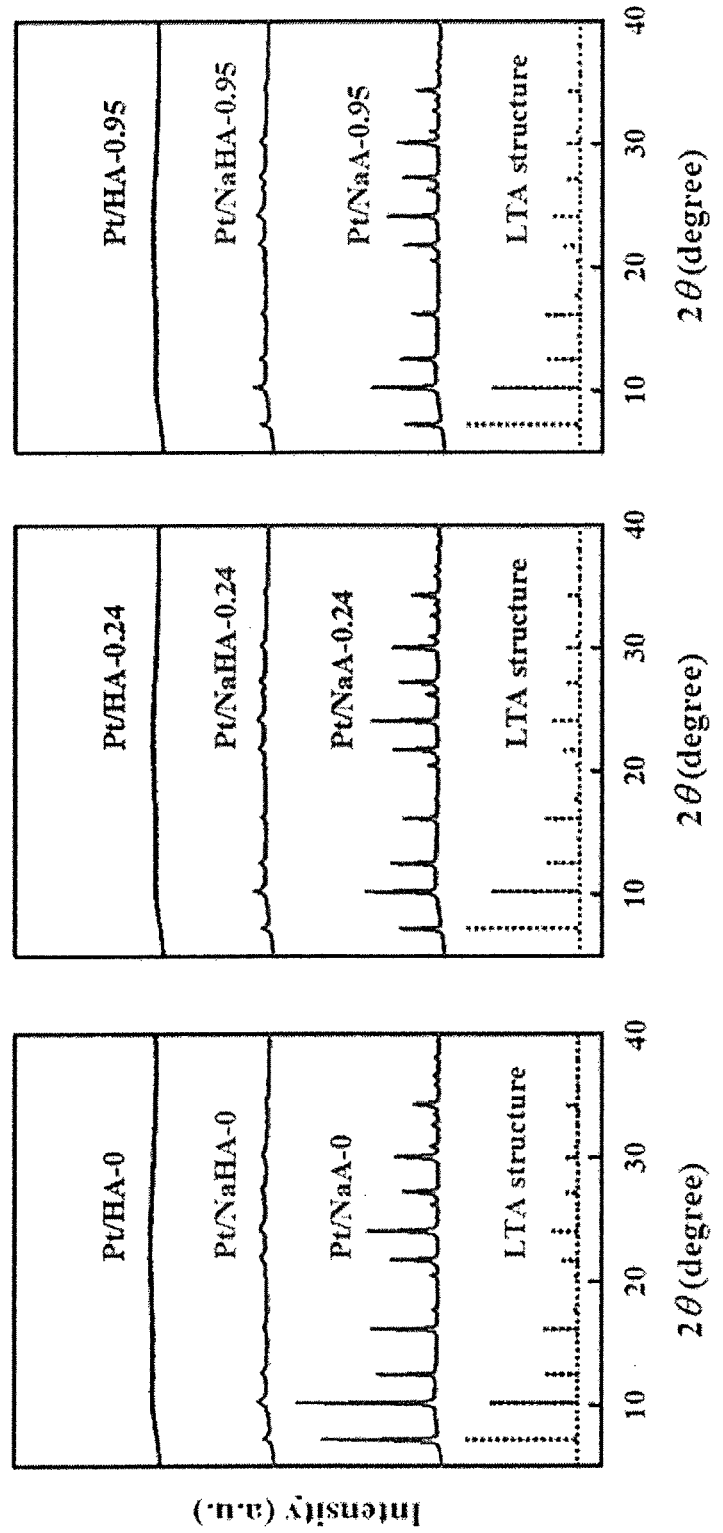
FIG. 3 is of graphs illustrating the results of XRD analysis of samples (Pt/NaA-0, Pt/NaA-0.24 and Pt/NaA-0.95) in which Pt is selectively encapsulated (supported) in NaA zeolites having various BET areas, samples (Pt/NaHA-0, Pt/NaHA-0.24 and Pt/NaHA-0.95) in which a Pt cluster is encapsulated (supported) in aluminosilicate formed by partial structural collapse of NaA zeolite, and samples (Pt/HA-0, Pt/HA-0.24 and Pt/HA-0.95) in which a Pt cluster is encapsulated (supported) in aluminosilicate formed by full structural collapse of NaA zeolite, in Example 1.

The results of XRD analysis of the crystal structures before/after collapse of zeolite are shown in FIG. 3. As illustrated in this drawing, the synthesized Pt-containing NaA zeolites showed the typical XRD pattern for LTA, and as the collapse of the crystal structure progressed, the peak intensity was gradually reduced (Pt/NaHA-0, Pt/NaHA-0.24 and Pt/NaHA-0.95). In the samples (Pt/HA-0, Pt/HA-0.24 and Pt/HA-0.95) including fully structurally collapsed zeolite, most of the crystal properties of zeolite disappeared. The main peak in NaA zeolite was 2θ=7.20, and the area of the main peak after collapse of zeolite was decreased to less than 0.8 of the area of the main peak before collapse. Briefly, $0.8(MainP_{zeolite})>(MainP_{collapse})$ is shown.

Analysis of $H_2$ and CO Chemisorption

Figure 4:
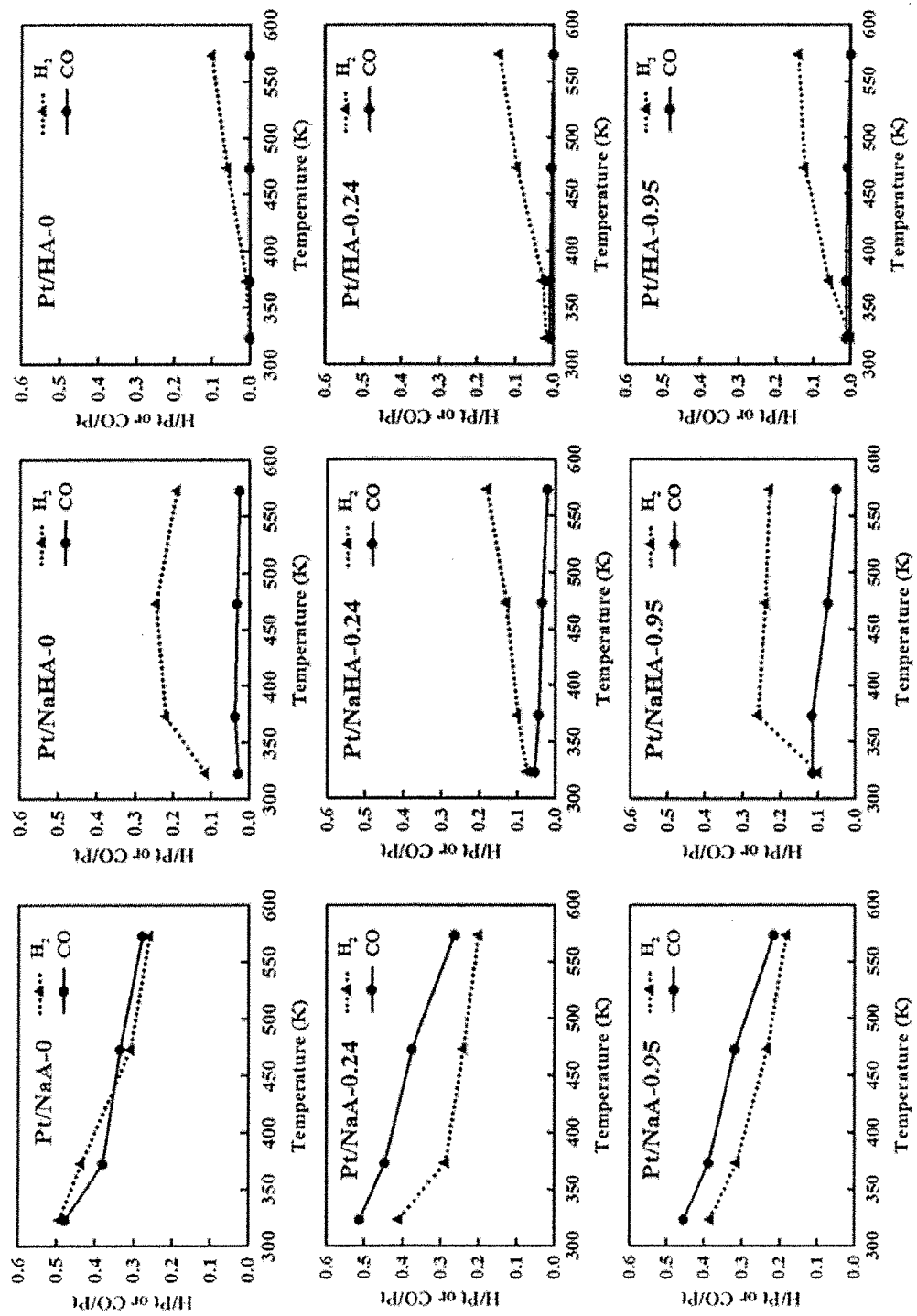
FIG. 4 is of graphs illustrating the $H_2$ and CO chemisorption results depending on the temperature in samples (Pt/NaA-0, Pt/NaA-0.24 and Pt/NaA-0.95) in which Pt is selectively encapsulated (supported) in NaA zeolites having various BET areas, samples (Pt/NaHA-0, Pt/NaHA-0.24 and Pt/NaHA-0.95) in which a Pt cluster is encapsulated (supported) in aluminosilicate formed by partial structural collapse of NaA zeolite, and samples (Pt/HA-0, Pt/HA-0.24 and Pt/HA-0.95) in which a Pt cluster is encapsulated (supported) in aluminosilicate formed by full structural collapse of NaA zeolite, in Example 1.

In individual zeolite catalyst samples having Pt encapsulated therein, the chemisorption behavior of hydrogen ($H_2$) and carbon monoxide (CO) depending on changes in the temperature is shown in FIG. 4, and $0.7*(H/Pt_{373}+H/Pt_{473}+H/Pt_{573})/3$ and $(CO/Pt_{373}+CO/Pt_{473}+CO/Pt_{573})/3$ are summarized in Table 3 below.

TABLE 3

| | Sample | A | B | Note |
|---|---|---|---|---|
| Before collapse | Pt/NaA-0 | 0.234 | 0.332 | A < B |
| | Pt/NaA-0.24 | 0.170 | 0.362 | |
| | Pt/NaA-0.95 | 0.171 | 0.307 | |
| After collapse (partial) | Pt/NaHA-0 | 0.152 | 0.031 | A > B |
| | Pt/NaHA-0.24 | 0.095 | 0.033 | |
| | Pt/NaHA-0.95 | 0.171 | 0.080 | |
| After collapse (full) | Pt/HA-0 | 0.039 | 0.000 | |
| | Pt/HA-0.24 | 0.062 | 0.004 | |
| | Pt/HA-0.95 | 0.075 | 0.007 | |
| | $Pt/SiO_2$ | 0.252 | 0.377 | A < B |

A: $0.7*(H/Pt_{373} + H/Pt_{473} + H/Pt_{573})/3$
B: $(CO/Pt_{373} + CO/Pt_{473} + CO/Pt_{573})/3$

In the samples before structural collapse of the zeolite, both the CO chemisorption amount and the hydrogen chemisorption amount were decreased in proportion to a rise in the adsorption temperature. However, in the samples including structurally collapsed zeolite, the CO chemisorption amount was totally decreased but the hydrogen chemisorption amount was increased, depending on the adsorption temperature rise. Specifically, in the samples (Pt/HA-0, Pt/HA-0.24 and Pt/HA-0.95) including fully structurally collapsed zeolite, molecular hydrogen could not diffuse up to the surface of the metal cluster dispersed in the aluminosilicate matrix at room temperature, in view of the hydrogen chemisorption amount at 323 K. Also, in the samples including fully structurally collapsed zeolite, the CO adsorption amount even at a raised temperature actually approximated to zero over the entire temperature range (<0.02). This is considered to be because CO has a larger molecular size (kinematic diameter: 0.38 nm) than a hydrogen atom.

Meanwhile, the partially collapsed samples (Pt/NaHA-0, Pt/NaHA-0.24 and Pt/NaHA-0.95) showed intermediate behavior between the samples before collapse and the fully collapsed samples, and manifested a predetermined hydrogen chemisorption amount at 323 K. In some samples (Pt/NaHA-0 and Pt/NaHA-0.95), the hydrogen adsorption amount was increased and then stagnated or slightly decreased depending on the temperature rise.

However, the samples including partially or fully structurally collapsed zeolite satisfied the relation of $0.7*(H/Pt_{373}+H/Pt_{473}+H/Pt_{573})/3>(CO/Pt_{373}+CO/Pt_{473}+CO/Pt_{573})/3$, whereas the samples in which zeolite was not structurally collapsed or the conventional catalyst ($Pt/SiO_2$) did not satisfy the above relation.

As is apparent from the results of analysis of chemisorption amounts, even when the zeolite structure is converted into a denser aluminosilicate matrix because of decationization during ion exchange and thermal treatment, the Pt cluster is still present to be encapsulated therein.

As illustrated in FIG. 2, as results of measurement of nitrogen adsorption for the fully collapsed samples, BET surface areas were 2 m² g⁻¹, 12 m² g⁻¹ and 33 m² g⁻¹ respectively, which were slightly lower than the specific surface areas of zeolite samples before collapse.

TEM Image

Figure 5:
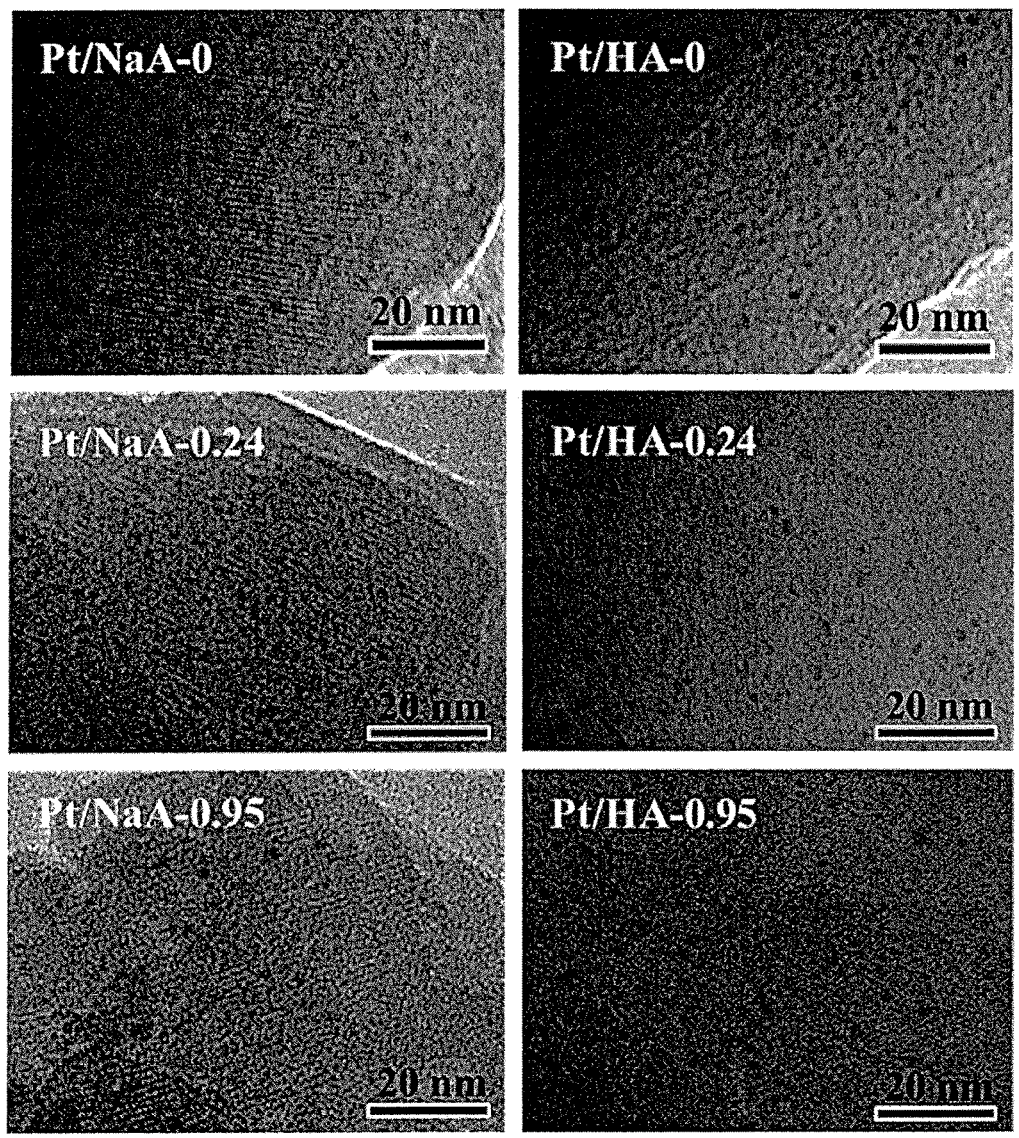
FIG. 5 illustrates TEM images of samples (Pt/NaA-0, Pt/NaA-0.24 and Pt/NaA-0.95) in which Pt is selectively encapsulated (supported) in NaA zeolites having various BET areas, and samples (Pt/HA-0, Pt/HA-0.24 and Pt/HA-0.95) in which a Pt cluster is encapsulated (supported) in aluminosilicate formed by full structural collapse of NaA zeolite, in Example 1.

To check whether metal (Pt) was uniformly encapsulated (supported) without size changes in the aluminosilicate matrix, TEM images for Pt/NaA-0, Pt/HA-0, Pt/NaA-0.24, Pt/HA-0.24, Pt/NaA-0.95 and Pt/HA-0.95 samples were analyzed. The results are shown in FIG. 5. As illustrated in this drawing, in the samples including structurally collapsed zeolite, the Pt cluster was efficiently dispersed in amorphous aluminosilicate. As such, the Pt cluster was observed to have a uniform diameter (about 1.0 nm).

EXAMPLE 2

Analysis of Solid-State Magic Angle Spinning Nuclear Magnetic Resonance (Solid-State MAS NMR)

Figure 6:
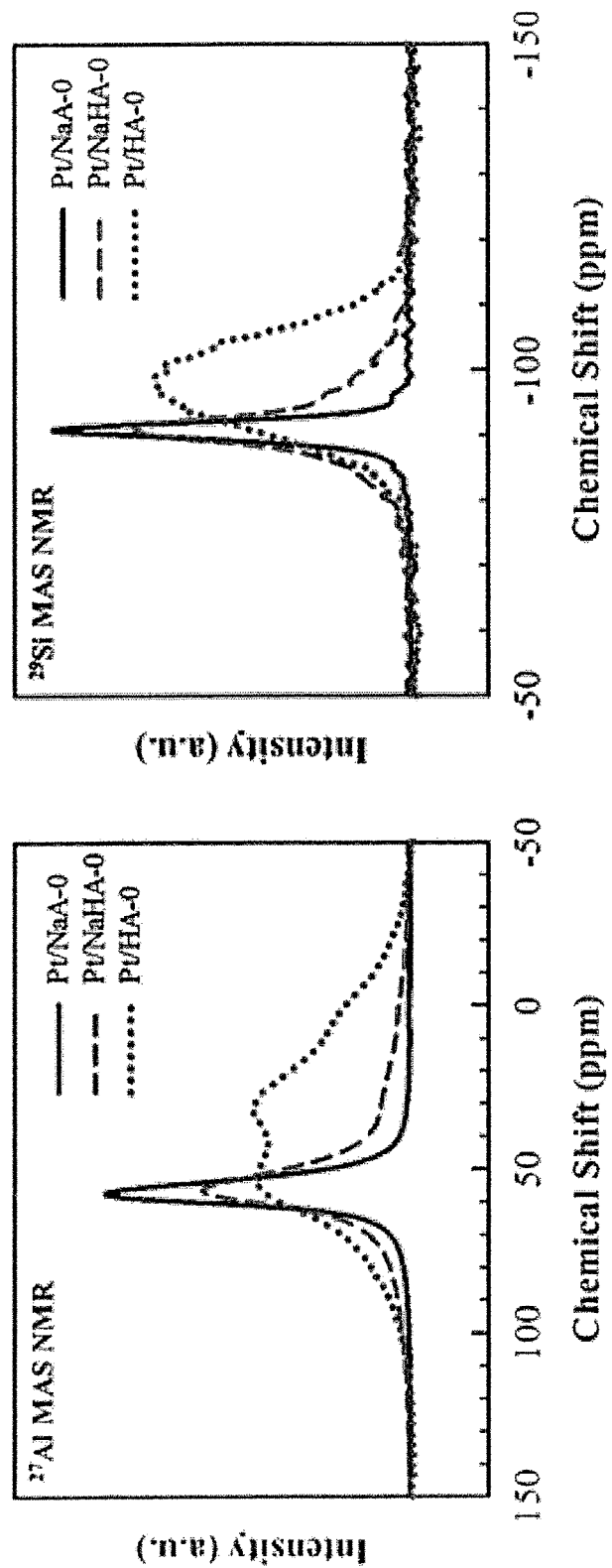
FIG. 6 is of graphs illustrating the results of nuclear magnetic resonance of a sample (Pt/NaA-0) in which Pt is selectively encapsulated (supported) in NaA zeolite, a sample (Pt/NaHA-0) in which a Pt cluster is encapsulated (supported) in aluminosilicate formed by partial structural collapse of NaA zeolite, and a sample (Pt/HA-0) in which a Pt cluster is encapsulated (supported) in aluminosilicate formed by full structural collapse of NaA zeolite, in Example 2.

The sample (Pt/NaA-0) in which Pt was supported in NaA zeolite and the samples (Pt/NaHA-0 and Pt/HA-0) in which Pt was supported in partially or fully structurally collapsed aluminosilicate were analyzed for $^{27}$Al MAS NMR and $^{29}$Si MAS NMR. The results are given in FIG. 6. Solid-state NMR spectra were recorded on a Bruker Avance 400 spectrometer with a widebore 9.4 $T$ magnet, operating at a Larmor frequency of 104.3 MHz ($^{27}$Al) and 79.5 MHz ($^{29}$Si). The magic angle spinning rates were set to 15 kHz and 5 kHz at $^{27}$Al and $^{29}$Si, respectively, and chemical shifts were recorded by a unit of ppm relative to standards of Al(NO₃)₃ and DSS (2,2-dimethyl-2-silapentane-5-sulfonic acid) for $^{27}$Al and $^{29}$Si, respectively.

As is apparent from the results of analysis of $^{27}$Al MAS NMR, as the structure collapsed, in the Pt/HA-0 sample, Al (60 ppm) having a tetrahedral structure was decreased and simultaneously penta-coordinated Al (25 ppm) and Al (0 ppm) having an octahedral structure were produced. On the other hand, as seen in the results of analysis of $^{29}$Si MAS NMR, as the structure collapsed, Si (−89 ppm) linked to four Al atoms was decreased, and very non-uniform Si structure (−80 ppm~−120 ppm) was thus produced. The partially structurally collapsed Pt/NaHA-0 sample showed a moderate tendency.

Whereas, in the Pt/NaA-0 sample, single narrow peaks were observed in both $^{27}$Al and $^{29}$Si MAS NMR spectra, which corresponded to tetrahedral Al (60 ppm) and Si (−89 ppm) linked to four Al atoms, respectively.

EXAMPLE 3

Analysis of Deactivation of Metal Surface by Sulfur

Figure 7:
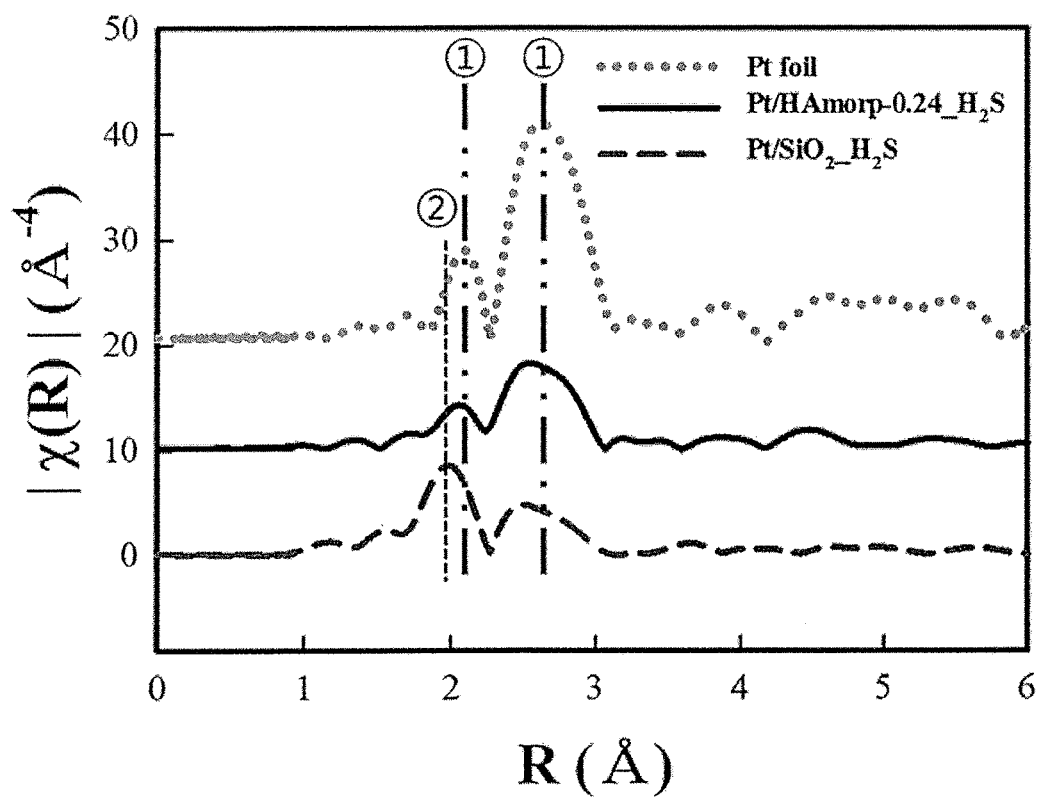
FIG. 7 is a graph illustrating the results (①; Pt—Pt coordination, ②; Pt—S coordination) of XAFS (X-ray absorption fine structure) analysis after respective $H_2S$ pretreatment of a sample (Pt/HA-0) in which a Pt cluster is encapsulated (supported) in aluminosilicate formed by full structural collapse of NaA zeolite, and a common $Pt/SiO_2$ sample, in Example 3.

To evaluate sulfur poisoning of the Pt catalyst supported in structurally collapsed amorphous aluminosilicate, formation of Pt—S bonding was observed by analysis of X-ray absorption fine structure (XAFS). The XAFS was analyzed in 7D-XAFS beamline at Pohang Accelerator Laboratory, and measured at Pt L3 edge in a transmission mode. Before the measurement, Pt/HA-0 and Pt/SiO₂ samples in an amount of about 0.3 g were compressed at 200 bar to thus manufacture pellets having a diameter of 13 mm, and such pellets were fitted to in-situ XAFS cells with 0.05 mm thick Al window. The samples fitted to the cells were pretreated at 573 K using 5% H₂S/H₂ (200 sccm) for 1 hr. The results of XAFS analysis are shown in FIG. 7 (①; Pt—Pt coordination and ②; Pt—S coordination).

As illustrated in this drawing, Pt/HA-0 showed radial distribution as in Pt foil, whereas Pt—S bonding was formed in the Pt/SiO₂ catalyst sample having externally exposed Pt. In the Pt/HA-0 sample, H₂S which is the simplest sulfur compound was inaccessible to the surface of metal (Pt).

EXAMPLE 4

Measurement of Benzene Hydrogenation Reactivity

Benzene hydrogenation was performed with the samples (Pt/NaA-0, Pt/NaA-0.24 and Pt/NaA-0.95) before structural collapse of zeolite and the samples (Pt/NaHA-0, Pt/NaHA-0.24, Pt/NaHA-0.95, Pt/HA-0, Pt/HA-0.24 and Pt/HA-0.95) having Pt supported in partially or fully structurally collapsed aluminosilicate.

Before the hydrogenation, to minimize effects of heat and mass transfer, each sample was mixed with gamma-alumina at a ratio of 1:9 and then molded (75~100 mesh), and thus used for the reaction as a final catalyst. The reaction was carried out using a mixture comprising 0.1 g of the catalyst and 1.9 g of SiO₂ by means of a fixed-bed continuous flow reactor, and all the samples were in-situ reduced at 673 K at an H₂ flow rate of 100 sccm before the reaction. Benzene hydrogenation was conducted under operating conditions (WHSV (h⁻¹)=525.9, 523 K, $P_{H2}$=472.54 kPa, and $P_{benzene}$=27.46 kPa).

Also, benzene hydrogenation was conducted by the same method with the conventional common catalyst (Pt/SiO₂) of Example 1.

Figure 8:
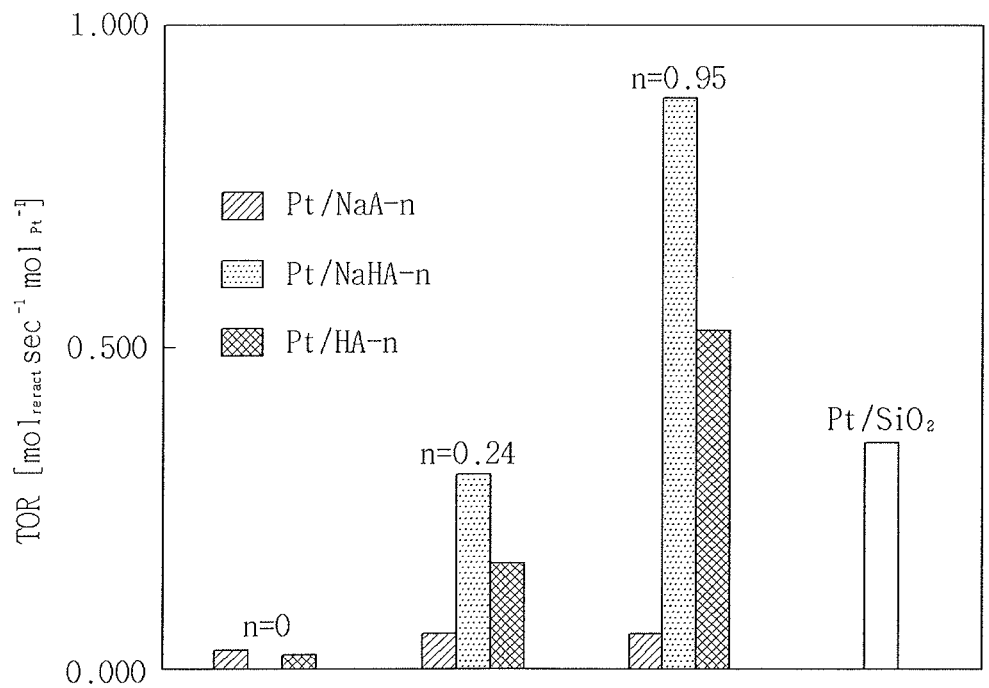
FIG. 8 is a graph illustrating benzene hydrogenation turnover rate (TOR) per total mol of Pt in samples (Pt/NaA-0, Pt/NaA-0.24 and Pt/NaA-0.95) in which Pt is selectively encapsulated (supported) in NaA zeolites having various BET areas, samples (Pt/NaHA-0, Pt/NaHA-0.24 and Pt/NaHA-0.95) in which a Pt cluster is encapsulated (supported) in aluminosilicate formed by partial structural collapse of NaA zeolite, samples (Pt/HA-0, Pt/HA-0.24 and Pt/HA-0.95) in which a Pt cluster is encapsulated (supported) in aluminosilicate formed by full structural collapse of NaA zeolite, and a common $Pt/SiO_2$ sample, in Example 4.

The activity of the catalyst may be represented by a turnover rate (TOR) per total mol of Pt in the catalyst or TOR per mol of Pt exposed to the surface as measured by hydrogen chemisorption at 323 K. The samples having Pt supported in the aluminosilicate matrix formed by full structural collapse of zeolite have infinite TOR because the hydrogen chemisorption amount is substantially zero at 323 K. Hence, comparison of the corresponding catalysts in which the hydrogen chemisorption amount at room temperature is actually zero with the common catalyst is regarded as inappropriate. In the present example, the evaluation was conducted based on TOR per total mol of Pt in the catalyst. The results are shown in FIG. 8.

As illustrated in this drawing, the activity was increased in proportion to an increase in the BET surface area. Among the samples having Pt supported in aluminosilicate formed by partial collapse of zeolite, the sample having a large specific surface area exhibited much higher hydrogenation activity compared to the conventional Pt/SiO₂ catalyst.

EXAMPLE 5

Measurement of Cyclohexane Dehydrogenation Reactivity

Cyclohexane dehydrogenation was performed with the samples (Pt/NaA-0, Pt/NaA-0.24 and Pt/NaA-0.95) before structural collapse of zeolite and the samples (Pt/NaHA-0, Pt/NaHA-0.24, Pt/NaHA-0.95, Pt/HA-0, Pt/HA-0.24 and Pt/HA-0.95) having Pt supported in partially or fully structurally collapsed aluminosilicate.

Before the dehydrogenation, to minimize effects of heat and mass transfer, each sample was mixed with gamma-alumina at a ratio of 1:9 and molded (75~100 mesh) and thus used for the reaction as a final catalyst. The reaction was carried out using a mixture of 0.1 g of the catalyst and 1.9 g of SiO₂ by means of a fixed-bed continuous flow reactor, and all the samples were in-situ reduced at 673 K at an H₂ flow rate of 100 sccm before the reaction. Cyclohexane underwent dehydrogenation under operating conditions (WHSV (h$^{-1}$)=467.4, 623 K, P$_{H2}$=92.45 kPa, and P$_{cyclohexane}$=7.55 kPa).

Figure 9:
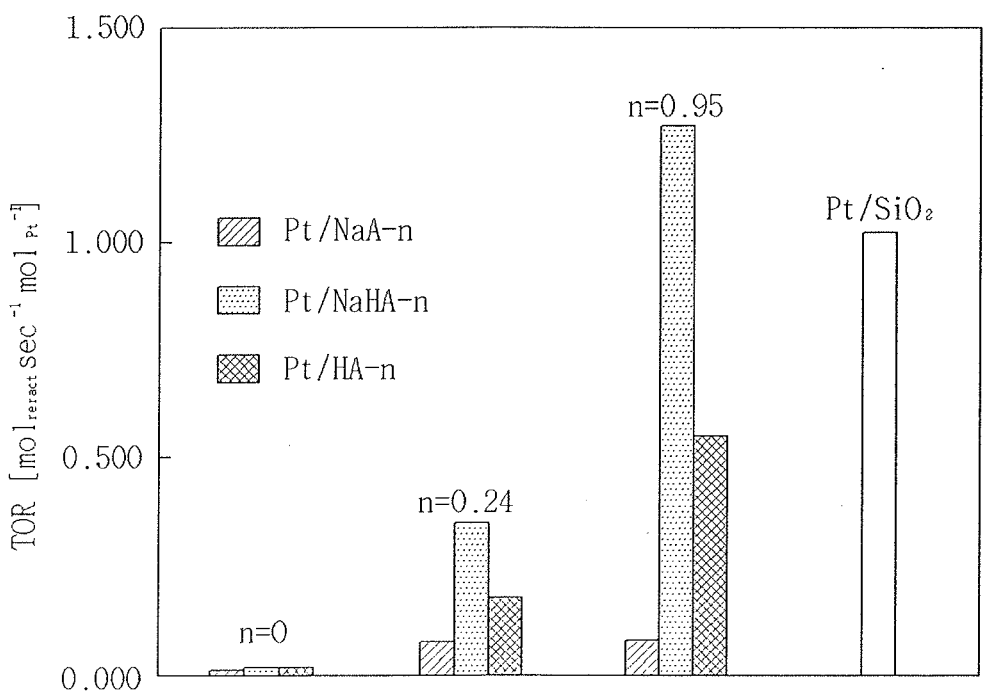
FIG. 9 is a graph illustrating cyclohexane dehydrogenation TOR per total mol of Pt in samples (Pt/NaA-0, Pt/NaA-0.24 and Pt/NaA-0.95) in which Pt is selectively encapsulated (supported) in NaA zeolites having various BET areas, samples (Pt/NaHA-0, Pt/NaHA-0.24 and Pt/NaHA-0.95) in which a Pt cluster is encapsulated (supported) in aluminosilicate formed by partial structural collapse of NaA zeolite, samples (Pt/HA-0, Pt/HA-0.24 and Pt/HA-0.95) in which a Pt cluster is encapsulated (supported) in aluminosilicate formed by full structural collapse of NaA zeolite, and a common $Pt/SiO_2$ sample, in Example 5.

Also, cyclohexane dehydrogenation was implemented by the same method with the conventional common catalyst (Pt/SiO$_2$) of Example 1. The results are shown in FIG. 9.

As illustrated in this drawing, the activity was increased in proportion to an increase in the BET surface area. Among the samples having Pt supported in aluminosilicate formed by partial collapse of zeolite, the sample having a large specific surface area exhibited much higher dehydrogenation activity compared to the conventional Pt/SiO$_2$ catalyst.

EXAMPLE 6

Measurement of Thiophene Hydrodesulfurization Reactivity

Thiophene hydrodesulfurization was performed with the samples (Pt/HA-0, Pt/HA-0.24 and Pt/HA-0.95) having Pt supported in fully structurally collapsed amorphous aluminosilicate. Before the reaction, to minimize effects of heat and mass transfer, each sample was mixed with gamma-alumina at a ratio of 1:9 and then molded (75~100 mesh) and thus used for the reaction as a final catalyst. The reaction was carried out using a mixture of 0.1 g of the catalyst and 1.9 g of SiO$_2$ by means of a fixed-bed continuous flow reactor, and all the samples were in-situ reduced at 673 K at an H$_2$ flow rate of 100 sccm before the reaction. Thiophene underwent hydrodesulfurization under operating conditions (WHSV (h$^{-1}$)=89.87, 573 K, P$_{H2}$=1976 kPa, P$_{thiophene}$=4 kPa, P$_{heptane}$=20 kPa).

Figure 10:
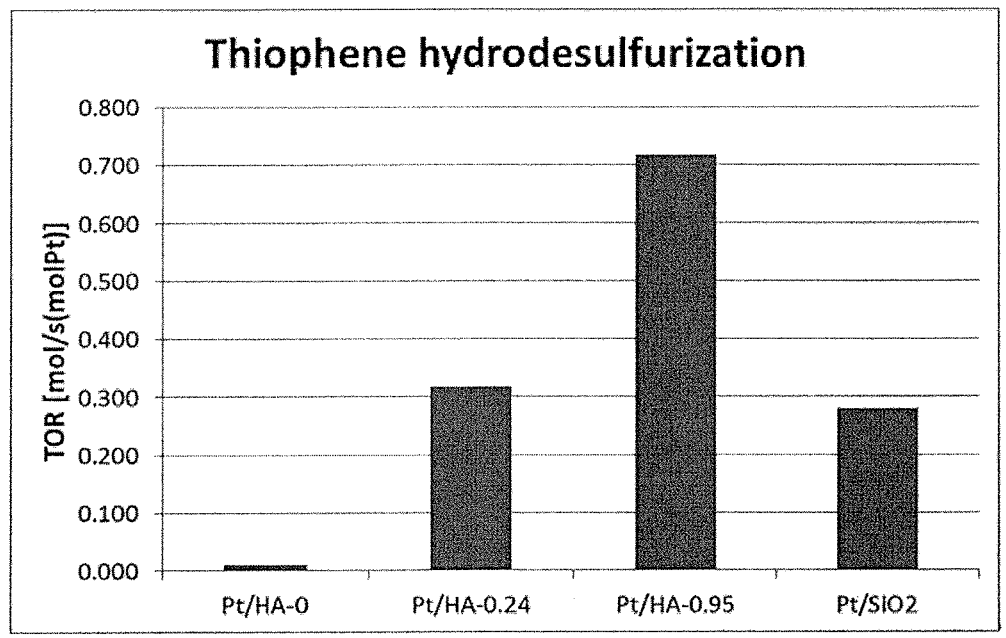
FIG. 10 is a graph illustrating thiophene hydrodesulfurization TOR per total mol of Pt in samples (Pt/HA-0, Pt/HA-0.24 and Pt/HA-0.95) in which a Pt cluster is encapsulated (supported) in aluminosilicate formed by full structural collapse of NaA zeolite, and a common $Pt/SiO_2$ sample, in Example 6.

Also, thiophene hydrodesulfurization was implemented by the same method with the conventional common catalyst (Pt/SiO$_2$) of Example 1. The results are shown in FIG. 10. As illustrated in this drawing, the hydrodesulfurization activity was increased in proportion to an increase in the BET surface area.

EXAMPLE 7

Measurement of Propane Hydrogenolysis Reactivity

Propane hydrogenolysis was performed with the samples (Pt/NaA-0, Pt/NaA-0.24 and Pt/NaA-0.95) before structural collapse of zeolite and the samples (Pt/NaHA-0, Pt/NaHA-0.24, Pt/NaHA-0.95, Pt/HA-0, Pt/HA-0.24 and Pt/HA-0.95) having Pt supported in partially or fully structurally collapsed aluminosilicate.

Before the propane hydrogenolysis, to minimize effects of heat and mass transfer, each sample was mixed with gamma-alumina at a ratio of 1:9 and molded (75~100 mesh) and thus used for the reaction as a final catalyst. The reaction was carried out using a mixture of 2 g of the catalyst and 2 g of SiO$_2$ by means of a fixed-bed continuous flow reactor, and all the samples were in-situ reduced at 673 K at an H$_2$ flow rate of 100 sccm before the reaction. Propane underwent hydrogenolysis under operating conditions (WHSV (h$^{-1}$)=5.41, 643 K, P$_{H2}$=40 kPa, P$_{He}$=50 kPa, P$_{propane}$=10 kPa).

Figure 11:
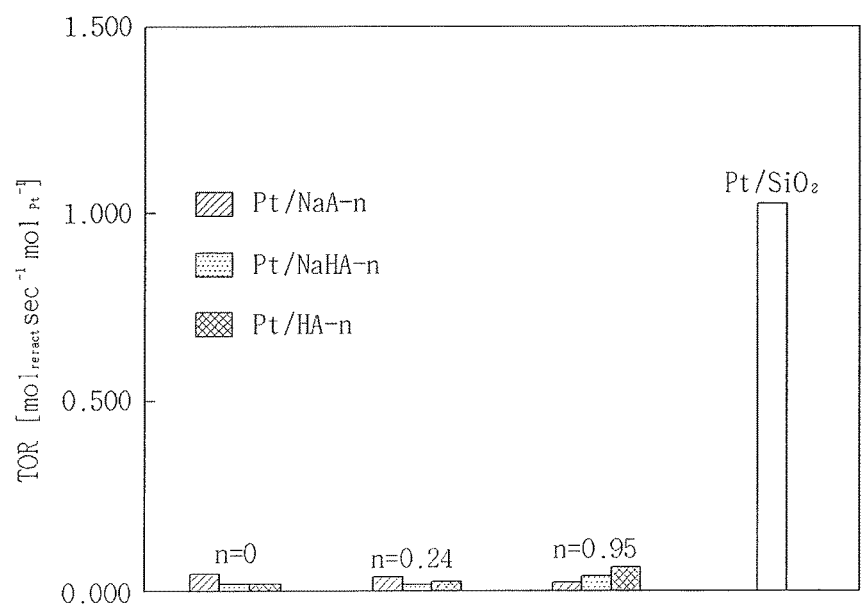
FIG. 11 is a graph illustrating propane hydrogenolysis TOR per total mol of Pt in samples (Pt/NaA-0, Pt/NaA-0.24 and Pt/NaA-0.95) in which Pt is selectively encapsulated (supported) in NaA zeolites having various BET areas, samples (Pt/NaHA-0, Pt/NaHA-0.24 and Pt/NaHA-0.95) in which a Pt cluster is encapsulated (supported) in aluminosilicate formed by partial structural collapse of NaA zeolite, samples (Pt/HA-0, Pt/HA-0.24 and Pt/HA-0.95) in which a Pt cluster is encapsulated (supported) in aluminosilicate formed by full structural collapse of NaA zeolite, and a common $Pt/SiO_2$ sample, in Example 7.

Also, propane hydrogenolysis was implemented by the same method with the conventional common catalyst (Pt/SiO$_2$) of Example 1. The results are shown in FIG. 11.

As illustrated in this drawing, the samples having Pt supported in structurally collapsed amorphous aluminosilicate had low propane hydrogenolysis activity regardless of the BET surface area. In particular, the activity was remarkably lower compared to the conventional common Pt/SiO$_2$ catalyst. In the case of the Pt/SiO$_2$ catalyst, high C—C hydrogenolysis activity is considered to result from an open pore structure thereof

EXAMPLE 8

Measurement of Propane Dehydrogenation Reactivity

Propane dehydrogenation was performed with the sample (Pt/NaHA-0.95) having partially structurally collapsed zeolite and the conventional common catalyst (Pt/SiO$_2$) of Example 1.

Figure 12:
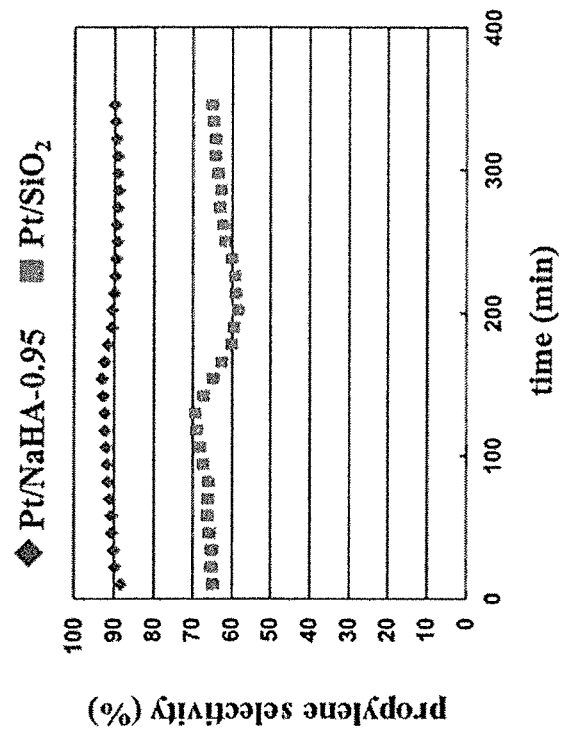
FIG. 12 is of graphs illustrating propane dehydrogenation TOR and propylene selectivity of a sample (Pt/NaHA-0.95) in which Pt is encapsulated (supported) in partially structurally collapsed amorphous aluminosilicate, and a common $Pt/SiO_2$ sample, in Example 8.
Figure 12:
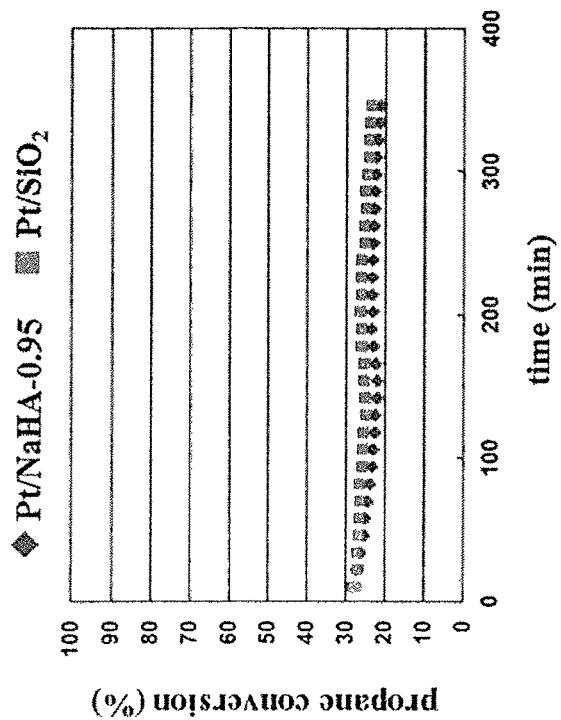

Before the propane dehydrogenation, to minimize effects of heat and mass transfer, each sample was mixed with gamma-alumina at a ratio of 1:9 and molded (75~100 mesh) and thus used for the reaction as a final catalyst. To compare selectivity in the same propane TOR range, a mixture comprising 4 g of the catalyst and 2 g of SiO$_2$ was used for Pt/NaHA-0.95, and a mixture comprising 5 g of the catalyst and 2 g of SiO$_2$ was used for Pt/SiO$_2$, and the reaction was carried out using a fixed-bed continuous flow reactor. All the samples were in-situ reduced at 823 K at an H$_2$ flow rate of 100 sccm before the reaction. Propane underwent dehydrogenation under operating conditions (823 K, P$_{H2}$=10 kPa, P$_{He}$=80 kPa, P$_{propane}$=10 kPa), and measurement was performed at WHSV (h$^{-1}$) of 2.7 and WHSV (h$^{-1}$) of 2.16 for Pt/NaHA-0.95 and Pt/SiO$_2$, respectively. The results are shown in FIG. 12.

As illustrated in this drawing, the sample (Pt/NaHA-0.95) having Pt supported in partially structurally collapsed amorphous aluminosilicate had significantly improved propylene selectivity in the same TOR range compared to the conventional common catalyst (Pt/SiO$_2$). Specifically, in the case of the sample (Pt/NaHA-0.95) having Pt supported in partially structurally collapsed amorphous aluminosilicate, the improved propylene selectivity is considered to result from much lower C—C hydrogenolysis activity thereof compared to the conventional common catalyst (Pt/SiO$_2$).

EXAMPLE 9

Evaluation of Metal Sintering by Thermal Treatment

Figure 13:
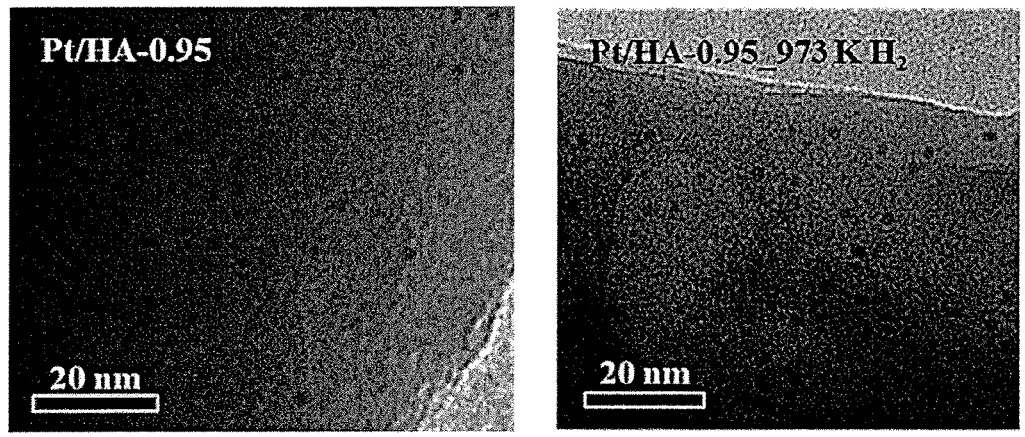
FIG. 13 illustrates TEM images before/after thermal treatment (973 K, 12 hr) of a Pt cluster in a sample (Pt/NaHA-0.95) in which Pt is encapsulated (supported) in fully structurally collapsed amorphous aluminosilicate, in Example 9.

The sample (Pt/HA-0.95) having Pt supported in fully structurally collapsed amorphous aluminosilicate was thermally treated at 973 K in an H$_2$ (200 sccm) atmosphere for 12 hr, after which sintering of Pt was observed by TEM (Transmission Electron Microscope). The TEM images before/after thermal treatment are illustrated in FIG. 13.

As seen in this drawing, the Pt/HA-0.95 sample was not increased in the size of Pt cluster even after thermal treatment of 12 hr, compared to before thermal treatment.

EXAMPLE 10

Selective Incorporation of Pt into Common NaX Zeolite

To dewater micropores of common NaX zeolite (13X molecular sieve, Sigma-Aldrich), thermal treatment was performed at 623 K for 6 hr in an air atmosphere, and Pt(NH$_3$)$_4$(NO$_3$)$_2$ (Aldrich) was used as the Pt precursor.

To selectively incorporate Pt into the micropores of common NaX zeolite, ion exchange at room temperature using a 0.002 M Pt(NH$_3$)$_4$(NO$_3$)$_2$ aqueous solution and then thermal treatment at 583 K, air atmosphere, 573 K, and H$_2$ atmosphere were implemented. As such, 25.9 ml of a 0.002 M Pt(NH$_3$)$_4$(NO$_3$)$_2$ aqueous solution per 1 g of NaX zeolite was used such that final Pt content was 1 wt %. The synthesized sample was denoted as Pt/NaX.

Structural Collapse of Zeolite by $NH_4^+$ Ion Exchange and Thermal Treatment

Pt/NaX zeolite synthesized by the above procedures was ion-exchanged with a 0.5 M ammonium nitrate ($NH_4NO_3$) solution at room temperature for 6 hr. Such ion exchange was performed three times using 140 ml of a 0.5 M ammonium nitrate ($NH_4NO_3$) solution per 1 g of Pt/NaX. The ion-exchanged sample was thermally treated at 573 K in an hydrogen atmosphere for 2 hr, and the degree of collapse of the zeolite crystal structure was analyzed by XRD. The sample subjected to ion exchange and then thermal treatment was denoted as Pt/HX.

XRD Analysis

Figure 14:
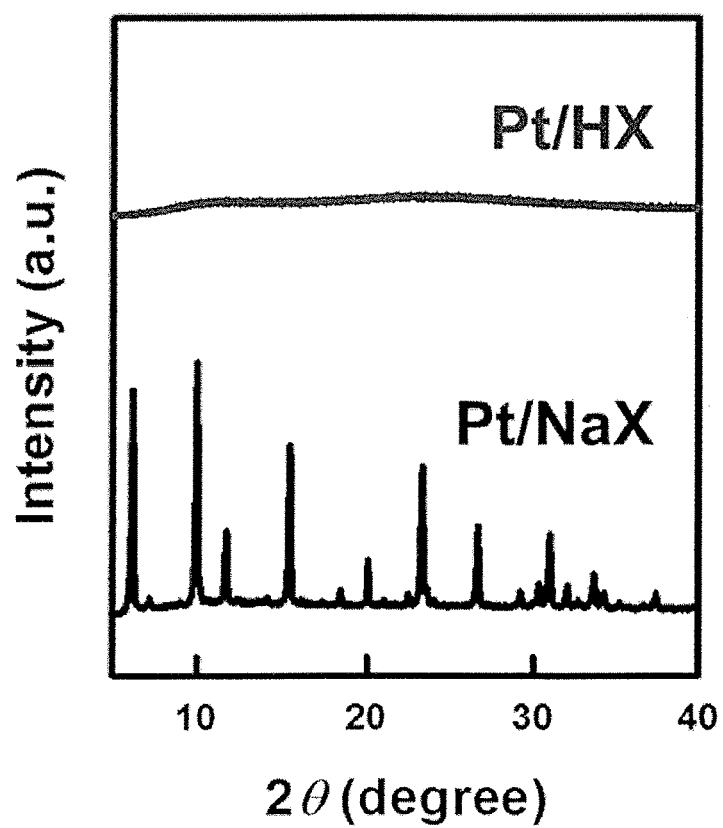
FIG. 14 is a graph illustrating the results of XRD analysis of a sample (Pt/NaX) in which a Pt cluster is encapsulated (supported) in common NaX zeolite and a sample (Pt/HX) in which a Pt cluster is encapsulated (supported) in aluminosilicate formed by full structural collapse of NaX zeolite, in Example 10.

The results of XRD analysis for the crystal structure before/after collapse of X-type zeolite are shown in FIG. 14. As illustrated in this drawing, the Pt-containing zeolite (Pt/NaX) showed the typical XRD pattern for FAU, whereas most of the crystal properties disappeared after collapse of the zeolite crystal structure (Pt/HX). In NaX zeolite, the main peak was 2θ=10, and the area of the main peak after structural collapse of zeolite was decreased to less than 0.8 of the area of the main peak before collapse. Briefly, the relation of $0.8(MainP_{zeolite})>(MainP_{collapse})$ was manifested.

Analysis of $H_2$ and CO Chemisorption

Figure 15:
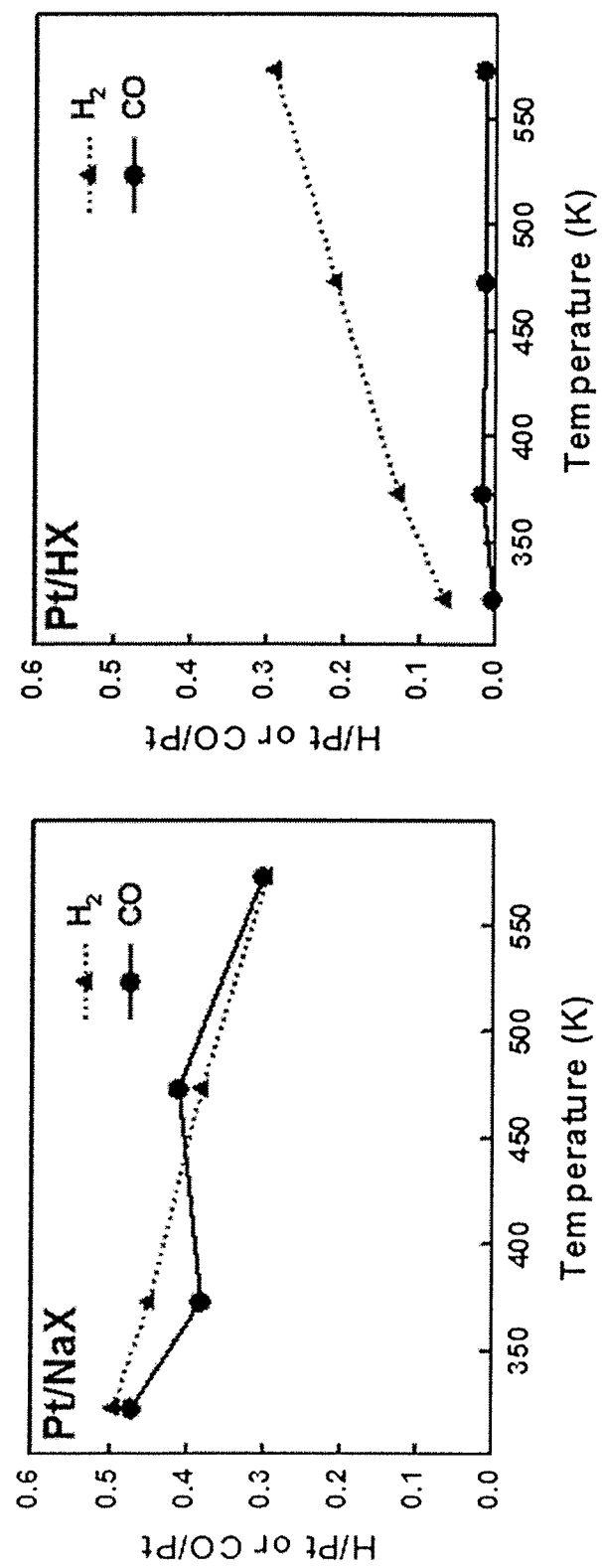
FIG. 15 is of graphs illustrating the results of $H_2$ and CO chemisorption depending on the temperature in a sample (Pt/NaX) in which a Pt cluster is encapsulated (supported) in common NaX zeolite and a sample (Pt/HX) in which a Pt cluster is encapsulated (supported) in aluminosilicate formed by full structural collapse of NaX zeolite, in Example 10.

As for Pt/NaX and Pt/HX samples, the chemisorption behavior of hydrogen ($H_2$) and carbon monoxide (CO) depending on changes in the temperature is shown in FIG. 15, and $0.7*(H/Pt_{373}+H/Pt_{473}+H/Pt_{573})/3$ and $(CO/Pt_{373}+CO/Pt_{473}+CO/Pt_{573})/3$ are summarized in Table 4 below.

TABLE 4

| Sample | A | B | Note |
|---|---|---|---|
| Pt/NaX | 0.262 | 0.363 | A < B |
| Pt/HX | 0.146 | 0.015 | A > B |

A: $0.7*(H/Pt_{373} + H/Pt_{473} + H/Pt_{573})/3$
B: $(CO/Pt_{373} + CO/Pt_{473} + CO/Pt_{573})/3$

As is apparent from the above table, X-type zeolite exhibited the relation of A>B after structural collapse of zeolite, as in A-type zeolite.

Analysis of Solid-State MAS NMR

Figure 16:
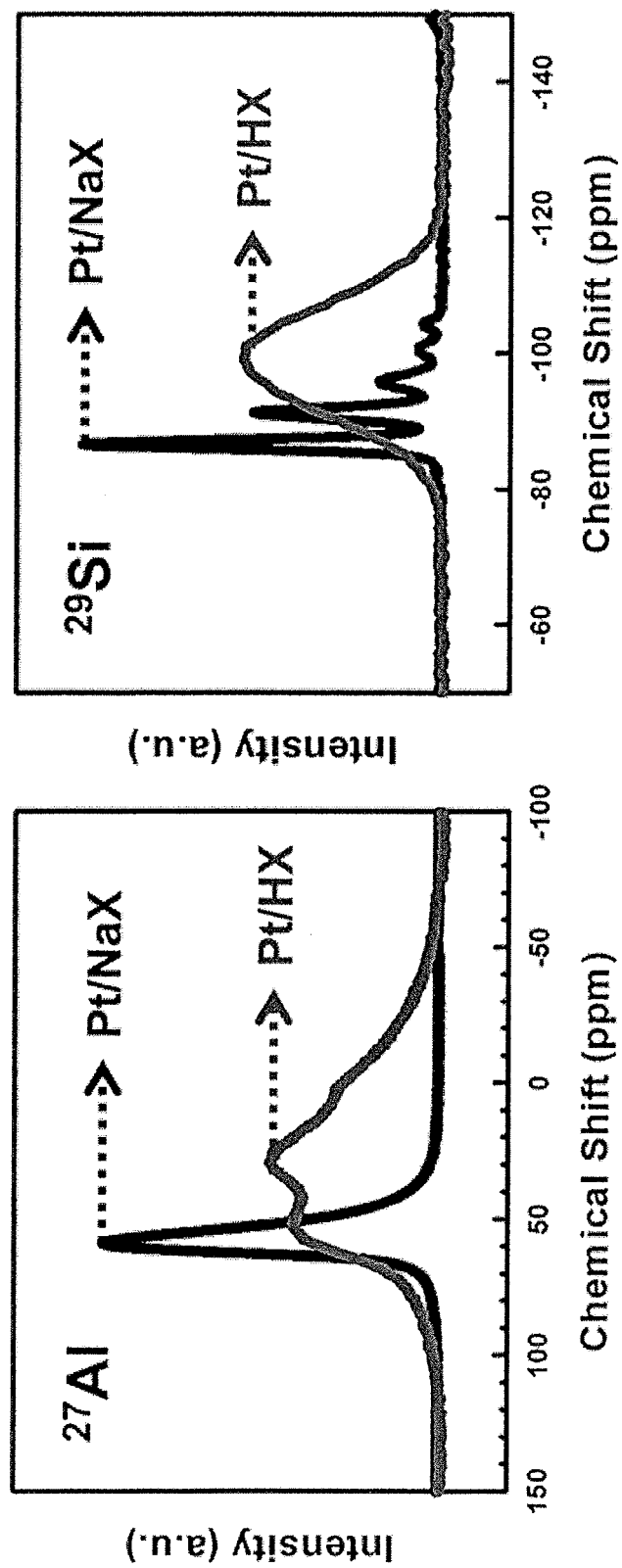
FIG. 16 is of graphs illustrating the results of nuclear magnetic resonance of a sample (Pt/NaX) in which a Pt cluster is encapsulated (supported) in common NaX zeolite and a sample (Pt/HX) in which a Pt cluster is encapsulated (supported) in aluminosilicate formed by full structural collapse of NaX zeolite, in Example 10.

The sample (Pt/NaX) having Pt supported in NaX zeolite and the sample (Pt/HX) having Pt supported in structurally collapsed aluminosilicate were analyzed for $^{27}Al$ MAS NMR and $^{29}Si$ MAS NMR. The results are shown in FIG. 16. Solid-state NMR spectra were recorded on a Bruker Avance 400 spectrometer with a widebore 9.4 T magnet, operating at a Larmor frequency of 104.3 MHz ($^{27}Al$) and 79.5 MHz ($^{29}Si$). The magic angle spinning rates were set to 15 kHz and 5 kHz at $^{27}Al$ and $^{29}Si$, and chemical shifts were recorded by a unit of ppm relative to standards of $Al(NO_3)_3$ and DSS (2,2-dimethyl-2-silapentane-5-sulfonic acid) for $^{27}Al$ and $^{29}Si$, respectively.

As is apparent from the results of analysis of $^{27}Al$ MAS NMR, as the structure collapsed, in the Pt/HX sample, Al (60 ppm) having a tetrahedral structure was decreased and simultaneously penta-coordinated Al (25 ppm) and Al (0 ppm) having an octahedral structure were produced. On the other hand, as seen in the results of analysis of $^{29}Si$ MAS NMR, as the structure collapsed, Si (−89 ppm) linked to four Al atoms was decreased, and very non-uniform Si (−80 ppm~−120 ppm) was thus produced.

Whereas, the Pt/NaX sample showed single narrow peaks in both $^{27}Al$ and $^{29}Si$ MAS NMR spectra, which corresponded to tetrahedral Al (60 ppm) and Si (−89 ppm) linked to four Al atoms, respectively.

EXAMPLE 11

Measurement of Benzene Hydrogenation Reactivity of Pt/NaX and Pt/HX

Benzene hydrogenation was performed with the sample (Pt/NaX) having Pt supported in NaX zeolite and the sample (Pt/HX) having Pt supported in structurally collapsed aluminosilicate.

Figure 17:
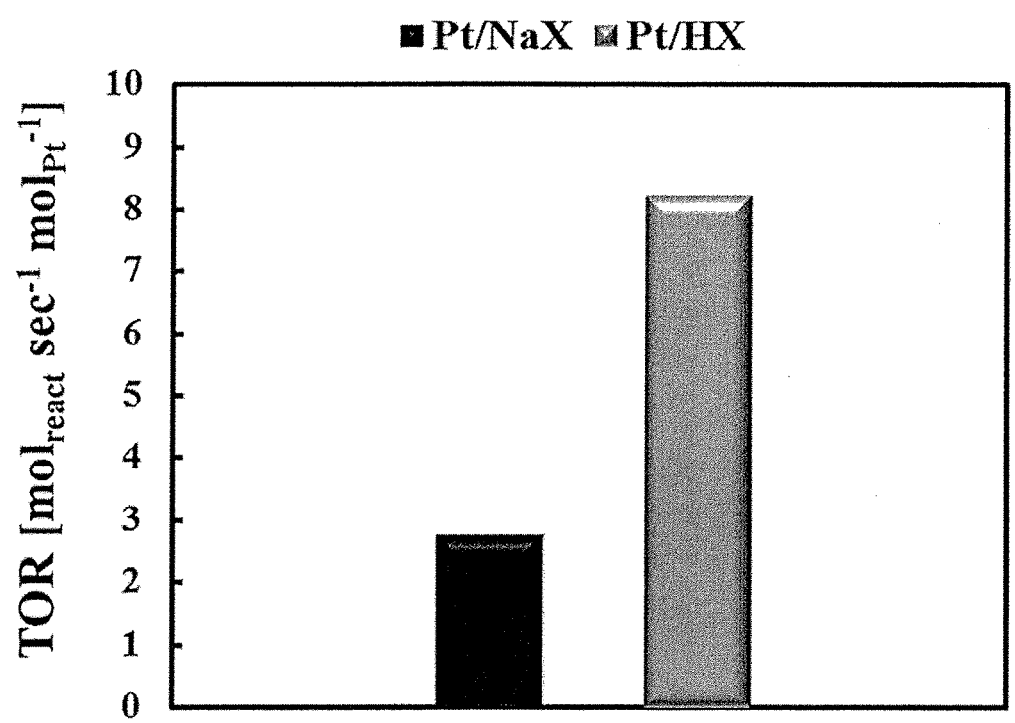
FIG. 17 is a graph illustrating benzene hydrogenation TOR per total mol of Pt in a sample (Pt/NaX) in which a Pt cluster is encapsulated (supported) in common NaX zeolite and a sample (Pt/HX) in which a Pt cluster is encapsulated (supported) in aluminosilicate formed by full structural collapse of NaX zeolite, in Example 11.

Before the hydrogenation, to minimize effects of heat and mass transfer, each sample was mixed with gamma-alumina at a ratio of 1:9 and then molded (75~100 mesh), and thus used for the reaction as a final catalyst. The reaction was carried out using a mixture comprising 0.2 g of the catalyst and 4 g of $SiO_2$ by means of a fixed-bed continuous flow reactor. All the samples were in-situ reduced at 573 K at an $H_2$ flow rate of 100 sccm before the reaction. Benzene underwent hydrogenation under operating conditions (WHSV ($h^{-1}$)=263.0, 523 K, $P_{H2}$=472.54 kPa, $P_{benzene}$=27.46 kPa). The results are shown in FIG. 17.

As illustrated in this drawing, the structurally collapsed Pt/HX catalyst exhibited higher hydrogenation reactivity compared to the Pt/NaX catalyst in which all reactants were accessible to the surface of metal.

EXAMPLE 12

Measurement of Propane Hydrogenolysis Reactivity of Pt/NaX and Pt/HX

Propane hydrogenolysis was performed with the sample (Pt/NaX) having Pt supported in NaX zeolite and the sample (Pt/HX) having Pt supported in structurally collapsed aluminosilicate.

Figure 18:
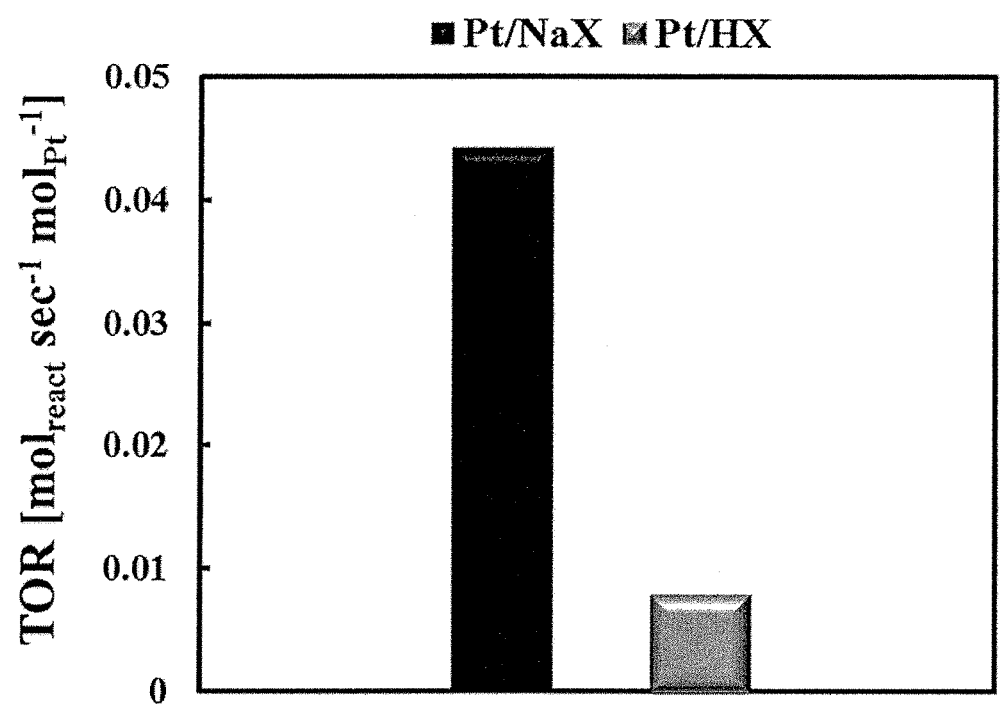
FIG. 18 is a graph illustrating propane hydrogenolysis TOR per total mol of Pt in a sample (Pt/NaX) in which a Pt cluster is encapsulated (supported) in common NaX zeolite and a sample (Pt/HX) in which a Pt cluster is encapsulated (supported) in aluminosilicate formed by full structural collapse of NaX zeolite, in Example 12.

Before the hydrogenolysis, to minimize effects of heat and mass transfer, each sample was mixed with gamma-alumina at a ratio of 1:9 and then molded (75~100 mesh), and thus used for the reaction as a final catalyst. The reaction was carried out using a mixture comprising 1.5 g of the catalyst and 4 g of $SiO_2$ by means of a fixed-bed continuous flow reactor, and all the samples were in-situ reduced at 723 K at an $H_2$ flow rate of 100 sccm before the reaction. Propane underwent hydrogenolysis under operating conditions (WHSV ($h^{-1}$)=3.60, 723 K, $P_{H2}$=90 kPa, $P_{propane}$=10 kPa). The results are shown in FIG. 18.

As illustrated in this drawing, the structurally collapsed Pt/HX catalyst exhibited much lower hydrogenolysis reactivity compared to the Pt/NaX catalyst in which all reactants were accessible to the surface of metal. In the case of the Pt/NaX catalyst, high C—C hydrogenolysis activity is considered to result from an open pore structure thereof

EXAMPLE 13

Measurement of Propane Dehydrogenation Reactivity of Pt/NaX and Pt/HX

Propane dehydrogenation was performed with the sample (Pt/NaX) having Pt supported in NaX zeolite and the sample (Pt/HX) having Pt supported in structurally collapsed aluminosilicate.

Figure 19:
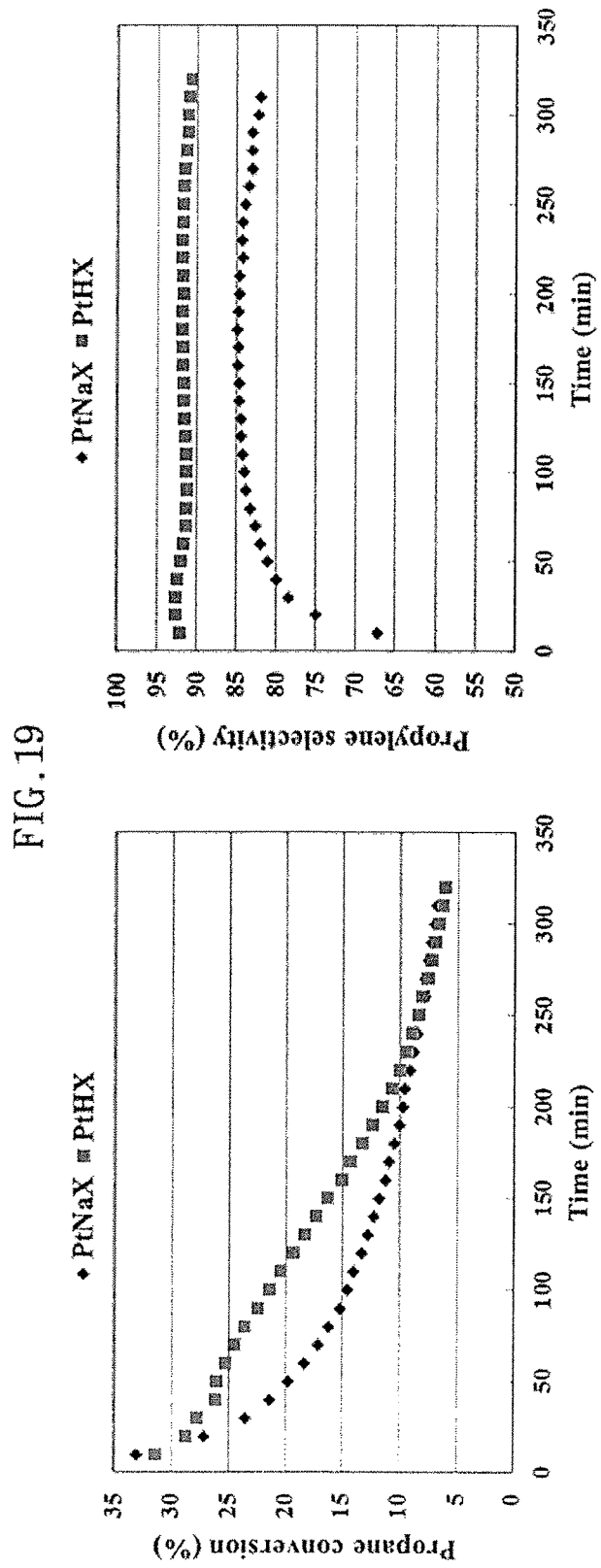
FIG. 19 is of graphs illustrating propane dehydrogenation TOR and propylene selectivity of a sample (Pt/NaX) in which a Pt cluster is encapsulated (supported) in common NaX zeolite and a sample (Pt/HX) in which a Pt cluster is encapsulated (supported) in aluminosilicate formed by full structural collapse of NaX zeolite, in Example 13.

Before the dehydrogenation, to minimize effects of heat and mass transfer, each sample was mixed with gamma-alumina at a ratio of 1:9 and then molded (75~100 mesh), and thus used for the reaction as a final catalyst. The reaction was carried out using a mixture comprising 2 g of the catalyst and 4 g of $SiO_2$ by means of a fixed-bed continuous flow reactor, and all the samples were in-situ reduced at 853 K at an $H_2$ flow rate of 100 sccm before the reaction. Propane underwent dehydrogenation under operating conditions (WHSV ($h^{-1}$)=7.21, 853 K, $P_{H2}$=10 kPa, $P_{He}$=70 kPa, $P_{propane}$=20 kPa). The results are shown in FIG. 19.

As illustrated in this drawing, the structurally collapsed Pt/FIX catalyst exhibited much higher propylene selectivity compared to the Pt/NaX catalyst in which all reactants were accessible to the surface of metal. However, the Pt/NaX catalyst having an open pore structure manifested high C—C hydrogenolysis activity and thus low propylene selectivity.

Accordingly, modifications or variations of the present invention may be easily utilized by those having ordinary knowledge in the art, and should also be understood as falling within the scope of the present invention.

The invention claimed is:

1. A hydrogen spillover-based catalyst, comprising:
crystalline or amorphous aluminosilicate formed by partial or full structural collapse of zeolite having a silica/alumina molar ratio of 2 or less, wherein the zeolite is P-type zeolite, A-type zeolite or X-type zeolite; and
a hydrogen activation metal (M) cluster encapsulated in the aluminosilicate,
wherein the hydrogen activation metal (M) cluster is incorporated into the zeolite using impregnation or ion-exchange, the metal cluster-incorporating zeolite is ion-exchanged with an ammonium ion ($NH_4^+$), and the ion-exchanged zeolite is thermally treated,
wherein changes in hydrogen and carbon monoxide chemisorption amounts depending on a temperature satisfy the following relation:

$0.7*(H/M_{373}+H/M_{473}+H/M_{573})/3 > (CO/M_{373}+CO/M_{473}+CO/M_{573})/3$ wherein H/M is a chemisorption amount (mol) of a hydrogen atom per total mol of M, CO/M is a chemisorption amount (mol) of carbon monoxide per total mol of M, and subscripts represent adsorption temperatures (K).

2. The hydrogen spillover-based catalyst of claim 1, wherein the silica/alumina molar ratio of zeolite is 1~2.

3. The hydrogen spillover-based catalyst of claim 1, wherein upon partial or full structural collapse of zeolite, an XRD (X-ray Diffraction) pattern of the catalyst shows the following:

$0.8(MainP_{zeolite}) > (MainP_{collapse})$ wherein $MainP_{zeolite}$ is a area of the highest peak among XRD peaks of zeolite before collapse, and $MainP_{collapse}$ is a base area of an XRD peak at the same 2θ of zeolite after collapse.

4. The hydrogen spillover-based catalyst of claim 1, wherein the hydrogen activation metal is any one or more selected from the group consisting of Groups IB, VIIB and VIII metals on a periodic table.

5. The hydrogen spillover-based catalyst of claim 1, wherein the metal cluster has a diameter of 0.5 ~50 nm.

6. The hydrogen spillover-based catalyst of claim 1, wherein an alkali metal/Al molar ratio in the aluminosilicate is 0.9 or less.

7. The hydrogen spillover-based catalyst of claim 1, wherein an alkaline earth metal/Al molar ratio in the aluminosilicate is 0.45 or less.

8. The hydrogen spillover-based catalyst of claim 1, wherein the amorphous aluminosilicate has micropores with a diameter of less than 0.29nm at room temperature.

* * * * *